United States Patent
Shah

(10) Patent No.: US 12,286,643 B2
(45) Date of Patent: *Apr. 29, 2025

(54) METHODS FOR GENERATING HEMATOPOIETIC STEM CELLS

(71) Applicant: The Brigham and Women's Hospital, Inc., Boston, MA (US)

(72) Inventor: Dhvanit I. Shah, Malden, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 685 days.

This patent is subject to a terminal disclaimer.

(21) Appl. No.: 16/972,212

(22) PCT Filed: Jun. 7, 2019

(86) PCT No.: PCT/US2019/035949
§ 371 (c)(1),
(2) Date: Dec. 4, 2020

(87) PCT Pub. No.: WO2019/236943
PCT Pub. Date: Dec. 12, 2019

(65) Prior Publication Data
US 2021/0222125 A1    Jul. 22, 2021

Related U.S. Application Data

(60) Provisional application No. 62/681,982, filed on Jun. 7, 2018.

(51) Int. Cl.
*C12N 5/0789* (2010.01)
*A61K 35/28* (2015.01)

(52) U.S. Cl.
CPC ............ *C12N 5/0647* (2013.01); *A61K 35/28* (2013.01); *C12N 2501/999* (2013.01); *C12N 2506/28* (2013.01); *C12N 2527/00* (2013.01)

(58) Field of Classification Search
CPC ... C12N 5/0647; C12N 2527/00; A61K 35/28
See application file for complete search history.

(56) References Cited

U.S. PATENT DOCUMENTS

| 11,597,913 | B2 | 3/2023 | Shah | |
|---|---|---|---|---|
| 2012/0195862 | A1* | 8/2012 | Daley | C12N 5/0634 435/377 |
| 2015/0004145 | A1 | 1/2015 | Lemischka et al. | |
| 2016/0003217 | A1 | 1/2016 | Allegretti | |
| 2016/0032317 | A1* | 2/2016 | Rossi | C12N 5/0647 435/456 |
| 2019/0119643 | A1 | 4/2019 | Daley et al. | |
| 2023/0041065 | A1 | 2/2023 | Shah et al. | |

FOREIGN PATENT DOCUMENTS

| CN | 108601356 A | 9/2018 |
|---|---|---|
| EP | 3383182 | 10/2018 |
| WO | WO 1999023205 | 5/1999 |
| WO | WO 2014/153069 | 9/2014 |
| WO | WO 2016/201133 A2 | 2/2016 |
| WO | WO 2016/201047 | 12/2016 |
| WO | WO 2017096215 | 6/2017 |
| WO | WO 2017/192708 | 11/2017 |
| WO | WO 2019/236943 | 12/2019 |
| WO | WO 2021/119061 | 6/2021 |

OTHER PUBLICATIONS

Kasper et al (Epigenetic and Epitranscriptomic Factors Make a Mark on Hematopoietic Stem Cell Development. Curr Stem Cell Rep. Mar. 2018 ; 4(1): 22-32) (Year: 2018).*
Lee (Biomechanical force in blood development: extrinsic physical cues drive pro-hematopoietic signaling. Differentiation. Oct. 2013 ; 86(3): 92-103; cited in IDS dated Jan. 12, 2021) (Year: 2013).*
Dunn (Flow-Dependent Epigenetic DNA Methylation in Endothelial Gene Expression and Atherosclerosis. Arterioscler Thromb Vasc Biol. 2015;35:1562-1569; cited in IDS dated Jan. 12, 2021) (Year: 2015).*
Sugimura et al (Haematopoietic stem and progenitor cells from human pluripotent stem cells. Nature, vol. 545, 2017; in IDS dated Jan. 12, 2021) (Year: 2017).*
Syeda et al (Chemical activation of the mechanotransduction channel Piezo1. eLife 2015;4:e07369; in IDS dated Jan. 12, 2021) (Year: 2015).*
North et al (Hematopoietic Stem Cell Development Is Dependent on Blood Flow. Cell 137, 736-748, May 15, 2009) (Year: 2009).*
Li et al (Piezo1 integration of vascular architecture with physiological force. Nature, vol. 515, 2014) (Year: 2014).*
Eppendorf Resources on Bioreactors (see in PTO-892) (Year: 2024).*
Berkels et al (Nifedipine and Bay K 8644 Induce an Increase of [Ca2+]I and Nitric Oxide in Endothelial Cells. J Cardiovasc Pharmacol Therapeut 4(3):175-181, 1999). (Year: 1999).*
Tokai et al (Genetic editing of HLA expression in hematopoietic stem cells to broaden their human application. Scientific Reports | 6:21757 | DOI: 10.1038/srep21757, 2016) (Year: 2016).*
Torikai et al (Toward eliminating HLA class I expression to generate universal cells from allogeneic donors. Blood, Aug. 22, 2013 x vol. 122, No. 8). (Year: 2013).*
SG Office Action in Singaporean Appln. No. 11202011962T, dated Aug. 1, 2022, 9 pages.

(Continued)

*Primary Examiner* — Emily A Cordas
*Assistant Examiner* — Matasha Dhar
(74) *Attorney, Agent, or Firm* — Fish & Richardson P.C.

(57) ABSTRACT

In some aspects and embodiments, the invention provides methods for making hematopoietic stem cells, including for HSCT. The method comprises providing a cell population comprising hemogenic endothelial (HE) or endothelial cells, and increasing activity or expression of DNA (cytosine-5-)-methyltransferase 3 beta (Dnmt3b) and/or GTPase IMAP Family Member 6 (Gimap6) in the HE and/or endothelial cells under conditions sufficient for stimulating formation of HSCs.

20 Claims, 17 Drawing Sheets

Specification includes a Sequence Listing.

(56) References Cited

OTHER PUBLICATIONS

Atilla et al., "A review of myeloablative vs reduced intensity/non-myeloablative regimens in allogeneic hematopoietic stem cell transplantations," Balkan Medical Journal, Jan. 1, 2017, 34(1):1-9.
AU Office Action in Australian Appln. No. 2019282761, dated May 19, 2023, 3 pages.
AU Office Action in Australian Appln. No. 2021240191, dated Jun. 13, 2023, 10 pages.
JP Japanese Office Action in Japanese Appln. No. 2020-567512, dated Jul. 4, 2023, 12 pages (with English translation).
Challen et al., "Dnmt3a and Dnmt3b have overlapping and distinct functions in hematopoietic stem cells." Cell Stem Cell, Sep. 4, 2014, 15(3):350-64.
Choi et al., "Identification of the hemogenic endothelial progenitor and its direct precursor in human pluripotent stem cell differentiation cultures." Cell Reports, Sep. 27, 2012, 2(3):553-67.
Coste et al., "Piezo1 and Piezo2 are essential components of distinct mechanically activated cation channels," Science, Oct. 1, 2010, 330(6000):55-60.
Ditadi et al., "Human definitive haemogenic endothelium and arterial vascular endothelium represent distinct lineages," Nature Cell Biology, May 2015, 17(5):580-91.
Dunn et al., "Flow-dependent epigenetic DNA methylation in endothelial gene expression and atherosclerosis," Arteriosclerosis, Thrombosis, and Vascular Biology, Jul. 2015, 35(7):1562-9.
Evans et al., "Yodal analogue (Dookul) which antagonizes Y odal-evoked activation of P iezo1 and aortic relaxation," British Journal of Pharmacology, May 2018, 175(10):1744-59.
Lacroix et al., "Probing the gating mechanism of the mechanosensitive channel Piezo 1 with the small molecule Yodal," Nature Communications, May 23, 2018, 9(1):1-3.
Lee et al., "Biomechanical force in blood development: extrinsic physical cues drive pro-hematopoietic signaling," Differentiation, Oct. 1, 2013, 86(3):92-103.
Lis et al., "Conversion of adult endothelium to immunocompetent haematopoietic stem cells," Nature, May 2017, 545(7655):439-45.
Moreau et al., "Viewpoint on the functionality of the human leukocyte antigen-G null allele at the fetal-maternal interface," Biology of Reproduction, Nov. 1, 2002, 67(5):1375-8.
Nakajima-Takagi et al., "Role of SOX17 in hematopoietic development from human embryonic stem cells," Blood, The Journal of the American Society of Hematology, Jan. 17, 2013, 121(3):447-58.
Park et al., "Efficient and simultaneous generation of hematopoietic and vascular progenitors from human induced pluripotent stem cells," Cytometry Part A, Jan. 2013, 83(1):114-26.
Pathak et al., "Stretch-activated ion channel Piezo1 directs lineage choice in human neural stem cells," Proceedings of the National Academy of Sciences, Nov. 11, 2014, 111(45):16148-53.
PCT International Preliminary Report on Patentability in International Appln. No. PCT/US2019/035949, Dec. 8, 2020, 11 pages.
PCT International Search Report and Written Opinion in International Appln. No. PCT/US2019/035949, Nov. 19, 2019, 22 pages.
Sandler et al., "Reprogramming human endothelial cells to haematopoietic cells requires vascular induction," Nature, Jul. 2014, 511(7509):312-8.
Slukvin, "Hematopoietic specification from human pluripotent stem cells: current advances and challenges toward de novo generation of hematopoietic stem cells," Blood, The Journal of the American Society of Hematology, Dec. 12, 2013, 122(25):4035-46.
Sugimura et al., "Haematopoietic stem and progenitor cells from human pluripotent stem cells," Nature, May 2017, 545(7655):432-8.
Syeda et al., "Chemical activation of the mechanotransduction channel Piezo1," Elife, May 22, 2015, 4:e07369, 11 pages.
Zambidis et al., "Expression of angiotensin-converting enzyme (CD143) identifies and regulates primitive hemangioblasts derived from human pluripotent stem cells," Blood, Nov. 1, 2008, 112(9):3601-14.
EP Supplementary European Search Report in European Appln. No. EP 19815158, dated Feb. 10, 2022, 7 pages.
Maneshi et al., "A microfluidic approach for studying piezo channels," Current Topics in Membranes, Jan. 1, 2017, 79:309-34.
Scapin et al., "A Bioreactor Simulating Pulse-Pressure Mediated Circumferential Stretch Stimulates Hematopoietic Stem Cell Formation," Blood, Dec. 2017, 130(Supplement 1):1142, 2 pages (abstract).
Scapin et al., "Piezo1-Sensitive Biomechanical Pulsation Stimulates Long-Term Hematopoietic Stem Cell Formation," Blood, Nov. 29, 2018, 132(Supplement 1):3826, 2 pages (abstract).
CN Office Action in Chinese Appln. No. 201980052501.5, mailed on Nov. 27, 2023, 10 pages (with English Translation).
Demirci et al., "Hematopoietic stem cells from pluripotent stem cells: Clinical potential, challenges, and future perspectives," Stem Cells Translational Medicine, Dec. 2020, 9(12):1549-57.
EP Extended European Search Report in European Appln. No. 20899010.1, mailed on Jan. 17, 2024, 13 pages.
Vincent et al., "TRPV4 agonists and antagonists," Current Topics in Medicinal Chemistry, Sep. 2011, 11(17):2216, 32 pages.
AU Office Action in Australian Appln. No. 2021240191, mailed on Jun. 13, 2023, 3 pages.
Bellin et al., "Induced pluripotent stem cells: the new patient?," Nature Reviews Molecular Cell Biology, Nov. 2012, 13(11):713-26.
Narsinh et al., "Comparison of human induced pluripotent and embryonic stem cells: fraternal or identical twins?," Molecular Therapy, Apr. 2011, 19(4):635-8.
Wang, "Myocardial Reprogramming Medicine: The Development, Application, and Challenge of Induced Pluripotent Stem Cells," New Journal of Science, Jun. 2014, vol. 2014, 23 pages.
CN Office Action in Chinese Appln. No. 202080096064.X, mailed on Mar. 9, 2024, 11 pages (with English translation).
JP Office Action in Japanese Appln. No. 2020-567512, mailed on Apr. 2, 2024, 6 pages (with English translation).
CN Office Action in Chinese Appln. No. 201980052501.5, mailed on Apr. 20, 2024, 10 pages (with English translation).
CN Office Action in Chinese Appln. No. 201980052501.5, mailed on Jun. 26, 2024, 12 pages (with English translation).
Daniel et al., "Making a hematopoietic stem cell," Trends in Cell Biology, Mar. 2016, 26(3):202-14.
JP Office Action in Japanese Appln. No. 2020-567512, mailed on Jun. 4, 2024, 6 pages (with English translation).
MX Office Action in Mexican Appln. No. MX/a/2020/013217, mailed on Jun. 3, 2024, 17 pages (with English translation).
KR Office Action in Korean Appln. No. 10-2018-7018396, mailed on Jul. 18, 2024, 7 pages (with English translation).
Burridge et al., "A universal system for highly efficient cardiac differentiation of human induced pluripotent stem cells that eliminates interline variability," PloS one, Apr. 2011, 6(4):e18293, 16 pages.
CN Office Action in Chinese Appln. No. 202080096064.X, mailed on Nov. 1, 2024, 13 pages (with English translation).
KR Office Action in Korean Appln. No. 10-2021-7000264, mailed on Oct. 28, 2024, 9 pages (with English translation).

* cited by examiner

METHODS FOR GENERATING HEMATOPOIETIC STEM CELLS

CLAIM OF PRIORITY

This application is a § 371 national stage application of International Application No. PCT/US2019/035949, filed on Jun. 7, 2019, which claims the benefit of U.S. Provisional Patent Application Ser. No. 62/681,982, filed on Jun. 7, 2018. The entire contents of the foregoing are hereby incorporated by reference.

FEDERALLY SPONSORED RESEARCH

This invention was made with Government support under Grant Nos. HL131645 DK085217, and DK100672 awarded by the National Institutes of Health. The Government has certain rights in the invention.

BACKGROUND

Hematopoietic stem cells (HSCs) are derived during embryogenesis in distinct regions where specific inductive events convert mesoderm to blood stem cells and progenitors. HSCs can give rise to both the myeloid and lymphoid lineages of blood cells in a process called hematopoiesis.

HSC transplantation (HSCT) is widely used to treat patients with blood, bone marrow, metabolic, and immune diseases. Despite advances in umbilical cord and haploidentical stem cell transplantation, the therapeutic use of HSC transplantation is often restricted due to the difficulty of finding suitable human leukocyte antigen (HLA)-matched donors in a timely manner, especially in countries with ethnic minorities and lack of national unrelated donor registries. Although mixed-race people account for 1.6 percent (9.7 million) of the U.S. population, multiracial volunteers make up only 3 percent (21,000) of the 7 million people on the registry, leaving 6,000 patients without a bone marrow match. Even if one finds a suitable match, immunologic complications such as graft-versus-host disease (GVHD), donor rejection, and high treatment-related mortality could compromise patient survival. However, these complications are eliminated by autologous transplant. Although autologous HSCs would not replace allogeneic HSCs entirely, especially in the context of hematologic malignancy, they would overcome major hurdles in HSCT including, lack of donor availability and GVHD for patients with a broad span of malignant and non-malignant hematologic, immune, and metabolic disorders.

Thus, there is a need for generating HSCs, including autologous HSCs, for HSCT.

SUMMARY

The present disclosure is based at least in part on the discovery that biomechanical and/or pharmacological activation of a mechanosensitive receptor (e.g., Piezo1) enhances Dnmt3b expression for hematopoietic stem cell (HSC) formation. As demonstrated herein, cdh5-morphant (cdh5-MO) embryos have a heartbeat-mediated pulsation in blood vessels without cardiac output and active blood flow. Pulsation-derived stretching activates Piezo1 mechanosensitive channels that further enhance Dnmt3b expression in the aorta-gonad-mesonephros (AGM) region to stimulate the hemogenic endothelial-to-HSC transition. The simulation of pulsation or the pharmacological activation of Piezo1 also yields three times higher amounts of HSCs, which reconstitute to normal, functional multi-lineage adult blood upon serial transplantation. In some embodiments, the hematopoietic stem cells produced according to this disclosure comprise long term hematopoietic stem cells (LT-HSCs), which exhibit superior engraftment, and reconstitute to functional, multi-lineage adult blood in the recipient.

In some aspects, the invention provides methods for making HSCs, the method comprising, providing a population comprising endothelial cells (e.g., hemogenic endothelial (HE) cells), and increasing activity or expression of DNA (cytosine-5-)-methyltransferase 3 beta (Dnmt3b) and/or GTPase IMAP Family Member 6 (Gimap6) in the cells under conditions sufficient for stimulating formation of HSCs. The HSCs can be recovered for administration to a patient.

In some embodiments, the endothelial cells are contacted with an effective amount of an agonist that increases the activity or expression of Dnmt3b. In some embodiments, the agonist is an agonist of a mechanosensitive receptor or a mechanosensitive channel. In some embodiments, the mechanosensitive receptor is Piezo1. An exemplary Piezo1 agonist is Yoda1. In some embodiments, the effective amount of the Yoda1 agonist is in the range of about 5 µM to about 200 µM, or about 5 µM to about 100 µM, or in some embodiments, about 25 µM to about 100 µM or about 25 µM to about 50 µM.

Alternatively, the activity or expression of Dnmt3b can be increased directly in the endothelial cells. For example, mRNA expression of Dnmt3b can be increased by delivering mRNA transcripts to the cells, or by introducing a Dnmt3b transgene and/or an episome, which may have one or more modifications thereto to increase or modify activity. In some embodiments, gene editing is employed to introduce a genetic modification to Dnmt3b expression elements in the endothelial or HE cells, such as to increase promoter strength, ribosome binding, or RNA stability.

In some embodiments, the invention comprises increasing the activity or expression of Gimap6 in the endothelial cells, alone or in combination with Dnmt3b. To increase activity or expression of Gimap6, Gimap6 mRNA transcripts can be introduced to the cells, or alternatively a Gimap6 transgene and/or an episome, and/or introducing a genetic modification of Gimap6 expression elements in the cells (such as one or more modifications to increase promoter strength, ribosome binding, or RNA stability).

In various embodiments, a cell population comprising the endothelial cells (e.g., hemogenic endothelial (HE) cells) is introduced to a bioreactor. In some embodiments, the bioreactor provides a cyclic-strain biomechanical stretching. The cyclic-strain biomechanical stretching increases the activity or expression of Dnmt3b and/or Gimap6. For example, a computer controlled vacuum pump system (e.g., the FlexCell™ Tension System, the Cytostretcher System, or similar) attached to a nylon, PDMS, or similar biocompatible biomimetic membrane of a flexible-bottomed culture plate can be used to apply 2D or 3D circumferential stretch ex vivo to HE cells under defined and controlled cyclic strain conditions.

In various embodiments, the HSC transition is induced by one or more selected from Piezo1 activation; mechanical stretching; introduction of an mRNA, with or without a transgene (i.e., transgene free), an episome, or genetic modification to Dnmt3b; and/or introduction of an mRNA, with or without a transgene (i.e., transgene free), an episome, or genetic modification to Gimap6.

In some embodiments, the HE cells are obtained or derived from induced pluripotent stem cells (iPSCs), non-hematopoietic stem cells, or somatic cells such as fibroblasts or endothelial cells. In some embodiments, the HE cells are obtained or derived from HLA-null cells, HLA-modified cells, and/or transgene-free cells, or from a genetic induction of endothelial cells to HE cells. The hemogenic endothelial cells (e.g., Flk1+CD45+ cells, Flk1+CD41+ cells or CD31+CD43+ cells) can be obtained in any manner, including derived from source cells of an allogeneic donor or from the subject to be treated with the HSC (i.e., by chemical, genetic, mRNA, transgene-free, or episome induction of autologous or allogenic cells to hemogenic endothelial cells. In some embodiments, HE cells are generated from iPSC created using cells from the recipient or a universal compatible donor). In some embodiments, developmentally plastic endothelial cells are employed.

In various embodiments, a pharmaceutical composition for cellular therapy is prepared that comprises a population of HSCs prepared by the methods described herein, and a pharmaceutically acceptable vehicle. The pharmaceutical composition may comprise at least about $10^2$ HSCs, or at least about $10^3$ HSCs, or at least about $10^4$ HSCs, or at least about $10^5$ HSCs, or at least about $10^6$ HSCs, or at least about $10^7$ HSCs, or at least $10^8$ HSCs. For example, in some embodiments, the pharmaceutical composition is administered, comprising from about 100,000 to about 400,000 HSCs per kilogram (e.g., about 200,000 cells/kg) of a recipient's body weight.

In some embodiments, a cellular therapy is prepared that comprises a population of HSCs prepared by the methods described herein. In some embodiments, the cellular therapy includes a pharmaceutically acceptable vehicle. The cellular therapy may comprise at least about $10^2$ HSCs, or at least about $10^3$ HSCs, or at least about $10^4$ HSCs, or at least about $10^5$ HSCs, or at least about $10^6$ HSCs, or at least about $10^7$ HSCs, or at least $10^8$ HSCs. For example, in some embodiments, the pharmaceutical composition is administered, comprising from about 100,000 to about 400,000 HSCs per kilogram (e.g., about 200,000 cells/kg) of a recipient's body weight. The number of HSC cells may be modified based on the age and weight of the patient.

The HSCs for transplantation can be generated in some embodiments in a relatively short period of time, such as less than about two months, or less than one about month (e.g., about 4 weeks), or less than about two weeks, or less than about one week, or less than about 6 days, or less than about 5 days, or less than about 4 days, or less than about 3 days. In some embodiments, the developmentally plastic endothelial or HE cells are cultured with increased Dnmt3b and/or Gimap6 activity or expression for 1 to 4 weeks.

HSCs prepared by the methods described herein are administered to a subject (a recipient), e.g., by intravenous infusion or intra-bone marrow transplantation. The methods can be performed following myeloablative, non-myeloablative, or immunotoxin-based (e.g. anti-c-Kit, anti-CD45, etc.) conditioning regimes.

The methods described herein can be used to generate populations of HSC for use in transplantation protocols, e.g., to treat blood (malignant and non-malignant), bone marrow, metabolic, and immune diseases. In some embodiments, the HSC populations are derived from autologous cells, e.g., generated from iPSC, which are created using cells from the recipient subject. In some embodiments, the HSC populations are derived from universally compatible donor cells or HLA-null hemogenic endothelial cells or similar cells conducive to become normal HSCs.

These and other aspects and embodiments of the invention are described by the following detailed description of the invention.

DETAILED DESCRIPTION

Figure 1A:
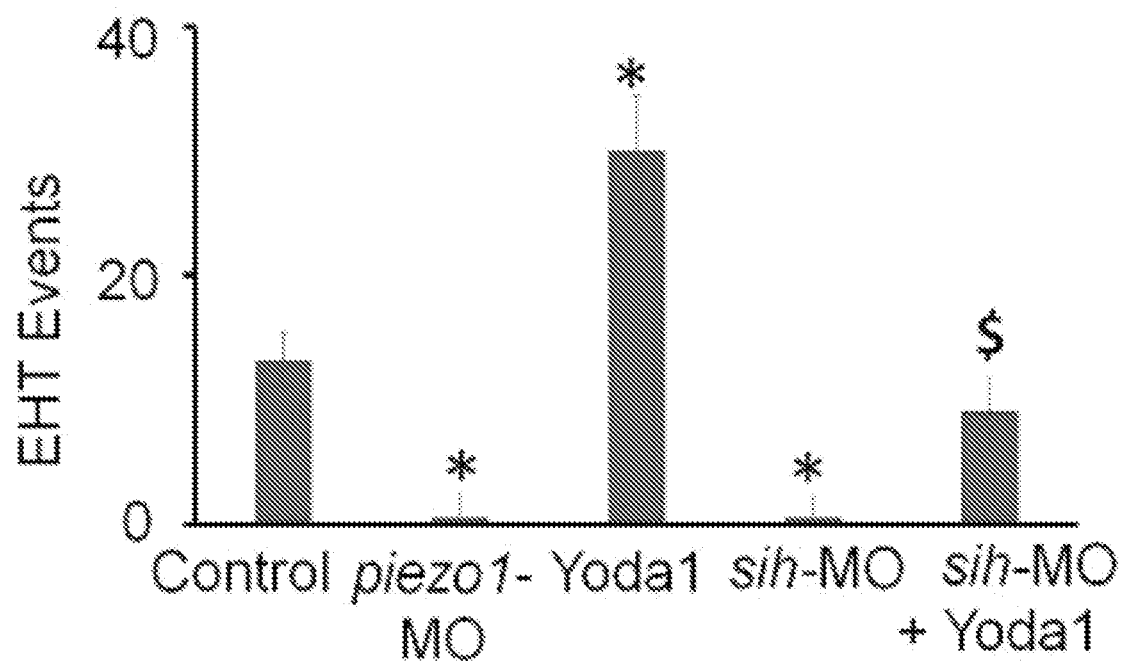
FIG. 1A shows time-lapse confocal imaging of cd41:eGFP+ HSCs emerging from flk1:mCherry+ endothelial cells in transgenic embryos between 26-42 hpf, the data demonstrates that the silencing of piezol attenuates the endothelial-to-HSC transition, whereas pharmacological activation of piezol (Yoda1) stimulates HSC formation in control embryos as well as rescues HSC formation in sih-MO embryos. n=5 per group. *P<0.05 vs. control; $P<0.05 vs. sih-MO.
Figure 1B:
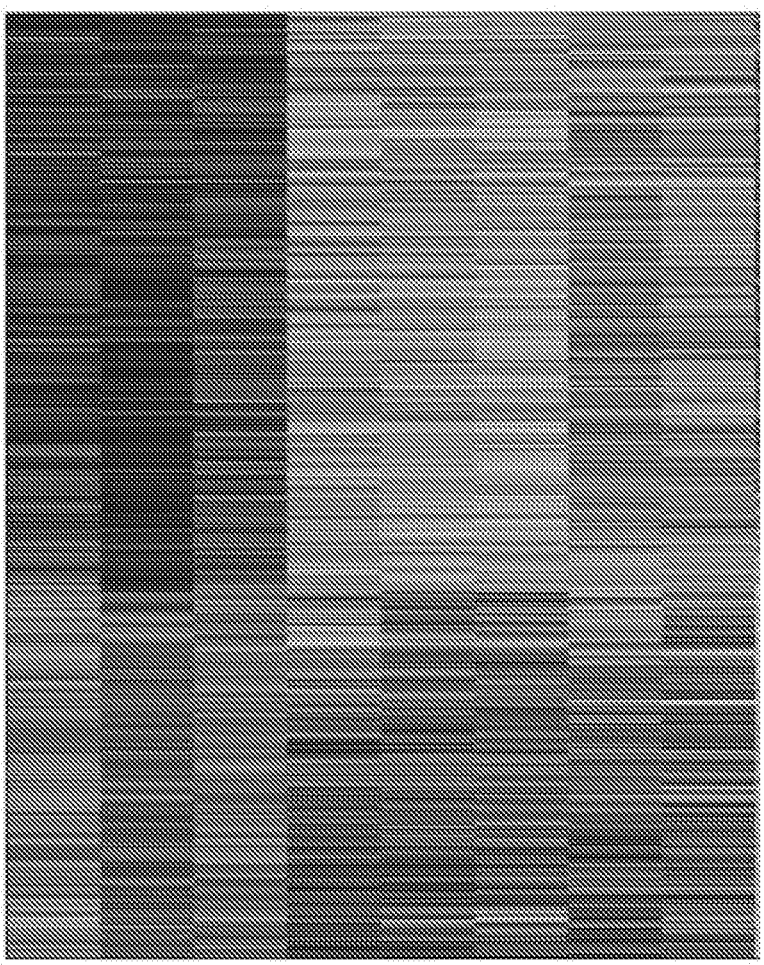
FIG. 1B is a heat map of differentially expressed genes in E11.5 AGM cells treated with cyclic strain, and Piezo1 activator (Yoda1); indicating that cyclic strain and Piezo1 activation have similar gene expression patterns in AGM during the endothelial-to-hematopoietic transition. n=3 per group.
Figure 1C:
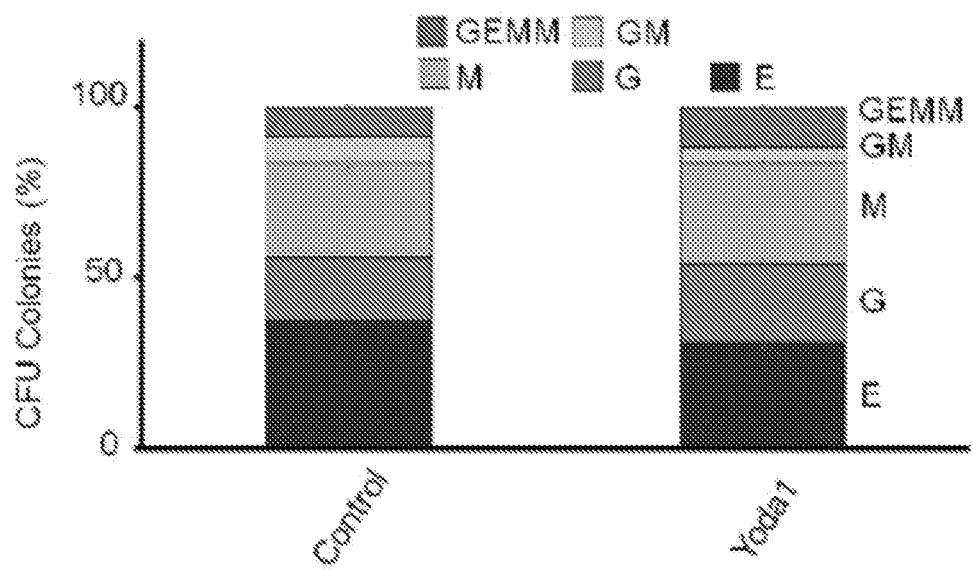
FIG. 1C shows a graph of hematopoietic colony formation unit (CFU) assays on E11.5 AGM cells, which demonstrates that Yoda1-mediated pharmacological activation of Piezo1 stimulates the endothelial-to-hematopoietic transition. n≥6 per group. *P<0.05 vs. Control. Abbreviations: GEMM (granulocyte, erythroid, macrophage, megakaryocyte); GM (granulocyte macrophage); G (granulocyte); M (macrophage); E (erythroid).

During fetal development, a subset of endothelial cells in the aorta-gonad-mesonephros (AGM) are hemogenic endothelial cells, which change their fate to become HSCs that ultimately colonize the fetal liver and bone marrow. However, the identities of the factors stimulating hemogenic endothelial cells remain elusive, limiting the utility of hemogenic endothelial cells as a potential source of functional HSCs. Blood flow-mediated shear-stress on the endothelial lining stimulates the endothelial emergence of HSCs. However, using Cdh5-null zebrafish and murine models, it was established that functional HSCs emerge despite early circulation arrest. Anderson H, et al., *Hematopoietic stem cells develop in the absence of endothelial cadherin 5 expression. Blood* 2015. These cdh5-silenced models were used in accordance with this disclosure as a pivot to study shear-stress and/or nitric oxide synthase (NOS)-independent biomechanical forces triggering functional HSC emergence, to investigate additional mechanisms by which pulse-pressure-mediated circumferential stretch governs HSC emergence.

Attempts to generate HSCs from hemogenic endothelial cells in the laboratory have been largely unsuccessful, in part due to a lack of knowledge about factors that stimulate HSC emergence from hemogenic endothelial cells. It is now established that circumferential vascular stretch due to pulsations from a beating heart triggers functional HSCs to emerge from hemogenic endothelial cells, which can ultimately engraft and differentiate into definitive lineages. In addition, the activation of stretch-sensitive transient receptor potential cation channel-subfamily vanilloid member 4 (Trpv4) channels rescued HSC formation in silent heart (tnnt2; sih)-silenced embryos in the absence of heartbeat and blood flow. See WO 2017/096215, which is hereby incorporated by reference in its entirety.

The present disclosure is based at least in part on the discovery that biomechanical and/or pharmacological activation of a mechanosensitive receptor (e.g., Piezo1) enhances Dnmt3b expression for hematopoietic stem cell (HSC) formation. As demonstrated herein, cdh5-morphant (cdh5-MO) embryos have a heartbeat-mediated pulsation in blood vessels without cardiac output and active blood flow. Pulsation-derived stretching activates Piezo1 mechanosensitive channels that further enhance Dnmt3b expression in the AGM to stimulate the endothelial-to-HSC transition. The simulation of pulsation or the pharmacological activation of Piezo1 also yields at least three times higher amounts of LT-HSCs, which reconstitute to normal, functional multi-lineage adult blood upon serial transplantation.

Accordingly, the results of the present disclosure demonstrate how heartbeat-mediated biomechanical forces stimulate cell-fate transitions and stem cell formation by activating mechanosensitive channels as well as epigenetic machinery. The development, expansion, and stemness maintenance of LT-HSCs are major challenges in HSC transplantation and cellular therapies for treating blood and bone marrow diseases. The present disclosure provides genetic and pharmacological targets to develop LT-HSCs.

In some aspects, the invention provides methods for making HSCs, the method comprising, providing a population comprising endothelial cells (e.g., HE cells), and increasing activity or expression of DNA (cytosine-5-)-methyltransferase 3 beta (Dnmt3b) and/or GTPase IMAP Family Member 6 (Gimap6) in the endothelial cells under conditions sufficient for stimulating formation of HSCs. The HSCs can be recovered for administration to a patient.

Dnmt3b (DNA (cytosine-5-)-methyltransferase 3 beta) is a DNA methyltransferase. Dnmt3b localizes primarily to the nucleus and its expression is developmentally regulated. Gimap6 is a member of the GTPases of immunity-associated proteins (GIMAP) family. GIMAP proteins contain GTP-binding and coiled-coil motifs.

In some embodiments, the endothelial cells are contacted with an effective amount of an agonist of a mechanosensitive receptor or a mechanosensitive channel that increases the activity or expression of Dnmt3b. In some embodiments, the mechanosensitive receptor is Piezo1. An exemplary Piezo1 agonist is Yoda1.

Yoda1 (2-[5-[[(2,6-Dichlorophenyl)methyl]thio]-1,3,4-thiadiazol-2-yl]-pyrazine) is a small molecule agonist developed for the mechanosensitive ion channel Piezo1. Syeda R, *Chemical activation of the mechanotransduction channel Piezo1*. eLife (2015). Yoda 1 has the following structure:

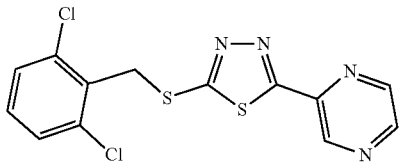 [SMILES: Clc1cccc(Cl)c1CCSc1nnc(-c2cnccn2)s1]

Derivatives of Yoda1 can be employed in various embodiments. For example, derivatives comprising a 2,6-dichlorophenyl core are employed in some embodiments. Exemplary agonists are disclosed in Evans E L, et al., *Yoda1 analogue (Dooku1) which antagonizes Yoda1-evoked activation of Piezo1 and aortic relaxation*, British J. of Pharmacology 175(1744-1759): 2018.

In some embodiments, the effective amount of the Yoda1 agonist or derivative is in the range of about 5 µM to about 500 µM, or about 5 µM to about 200 µM, or about 5 µM to about 100 µM, or in some embodiments, in the range of about 25 µM to about 150 µM, or about 25 µM to about 100 µM, or about 25 µM to about 50 µM.

Alternatively, the activity or expression of Dnmt3b can be increased directly in the endothelial or HE cells. For example, mRNA expression of Dnmt3b can be increased by delivering Dnmt3b-encoding transcripts to the cells, or by introducing a Dnmt3b-encoding transgene, or a transgene-free method, not limited to introducing an episome to the cells, which may have one or more nucleotide modifications (or encoded amino acid modifications) thereto to increase or modify activity. In some embodiments, gene editing is employed to introduce a genetic modification to Dnmt3b expression elements in the endothelial cells, such as to increase promoter strength, ribosome binding, RNA stability, or impact RNA splicing.

In some embodiments, the invention comprises increasing the activity or expression of Gimap6 in the endothelial cells, alone or in combination with Dnmt3b and/or other modified genes upon cyclic strain or Piezo1 activation. To increase activity or expression of Gimap6, Gimap6-encoding mRNA transcripts can be introduced to the cells, transgene-free approaches can also be employed, including but not limited, to introducing an episome to the cells; or alternatively a Gimap6-encoding transgene, which may have one or more nucleotide modifications (or encoded amino acid modifications) thereto to increase or modify activity. In some embodiments, gene editing is employed to introduce a genetic modification to Gimap6 expression elements in the endothelial cells (such as one or more modifications to increase promoter strength, ribosome binding, RNA stability, or to impact RNA splicing).

In some embodiments, mRNA and/or episome(s) (e.g., encoding Dnmt3b or Gimap6) is produced synthetically, such as by direct chemical synthesis or in vitro transcription, and introduced into endothelial cells. Known chemical modifications can be used to avoid the innate-immune response in the cells. For example, synthetic RNA comprising only canonical nucleotides can bind to pattern recognition receptors, and can trigger a potent immune response in cells. This response can result in translation block, the secretion of inflammatory cytokines, and cell death. RNA comprising certain non-canonical nucleotides can evade detection by the innate immune system, and can be translated at high efficiency into protein. See U.S. Pat. No. 9,181,319, which is hereby incorporated by reference, particularly with regard to nucleotide modification to avoid an innate immune response. mRNA can be introduced into the cells by known methods once or periodically during HSC production.

In some embodiments, expression of Dnmt3b and/or Gimap6 is increased by introducing a transgene into the cells, which can direct a desired level of over expression (with various promoter strengths or other selection of expression control elements). Transgenes can be introduced using various viral vectors or transfection reagents known in the art. In some embodiments, expression of Dnmt3b and/or Gimap6 is increased by a transgene-free method (e.g., episome delivery).

In some embodiments, expression or activity of Dnmt3b and/or Gimap6 are increased using a gene editing technology, for example, to introduce one or more modifications to increase promoter strength, ribosome binding, or RNA stability. Various editing technologies are known, and include CRISPR, zinc fingers (ZFs) and transcription activator-like effectors (TALEs). In some embodiments, expression or activity of Dnmt3b and/or Gimap6 is increased by a transgene-free method (e.g., episome delivery). Fusion proteins containing one or more of these DNA-binding domains and the cleavage domain of Fok1 endonuclease can be used to create a double-strand break in a desired region of DNA in a cell (See, e.g., US Patent Appl. Pub. No. US 2012/0064620, US Patent Appl. Pub. No. US 2011/0239315, U.S. Pat. No. 8,470,973, US Patent Appl. Pub. No. US 2013/0217119, U.S. Pat. No. 8,420,782, US Patent Appl. Pub. No. US 2011/0301073, US Patent Appl. Pub. No. US 2011/0145940, U.S. Pat. Nos. 8,450,471, 8,440,431, 8,440,432, and US Patent Appl. Pub. No. 2013/0122581, the contents of all of which are hereby incorporated by reference). In some embodiments, gene editing is conducting using CRISPR associated Cas system, as known in the art. See, for example, U.S. Pat. Nos. 8,697,359, 8,906,616, and 8,999,641, which is hereby incorporated by reference in its entirety.

In various embodiments, a cell population comprising developmentally plastic endothelial or HE cells is introduced to a bioreactor. In some embodiments, the bioreactor provides a cyclic-strain biomechanical stretching, as described in WO 2017/096215, which is hereby incorporated by reference in its entirety. The cyclic-strain biomechanical stretching increases the activity or expression of Dnmt3b and/or Gimap6. In these embodiments, mechanical means apply stretching forces to the cells. For example, a computer controlled vacuum pump system (e.g., the Flex-Cell™ Tension System, the Cytostretcher System, or similar) attached to a nylon or similar biocompatible and biomimetic membrane of a flexible-bottomed culture plate can be used to apply 2D or 3D circumferential stretch ex vivo to HE cells under defined and controlled cyclic strain conditions.

In various embodiments, the HSC transition is induced by at least means selected from Piezo1 activation, mechanical stretching, introduction of an mRNA, transgene, transgene-free (e.g., episome), or genetic modification to Dnmt3b, and/or introduction of an mRNA, transgene, transgene-free (e.g., episome), or genetic modification to Gimap6.

The HE cells can be obtained or derived from a subject who has a blood, bone marrow, metabolic, or immune disease. In some embodiments, the subject does not have a hematological malignancy. The population of HSCs can be administered to a recipient. For autologous HSC transplantation, the HE cells will have been derived from the recipient.

In some embodiments, the HE cells are obtained or derived from induced pluripotent stem cells (iPSCs), non-hematopoietic stem cells, or somatic cells, including but not limited to fibroblasts and endothelial cells. In some embodiments, the HE cells are obtained or derived from HLA-null cells, HLA-modified cells, and/or transgene-free cells, or from a genetic induction of endothelial cells to HE cells. The hemogenic endothelial cells (e.g., Flk1+CD45+ cells, Flk1+CD41+ cells or CD31+CD43+ cells) can be obtained in any manner, including from source cells from an allogeneic donor or from the subject to be treated with the HSC. For example, HE cells may be obtained by chemical, genetic, transgene-free, or episome induction of autologous or allogenic cells to hemogenic endothelial cells. In some embodiments, HE cells are generated from iPSC created from cells of the recipient, or from cells that are HLA-modified, or from cells that are HLA-null cells. In some embodiments, the HE cells are obtained or derived from cells of a subject, wherein the subject is a universally compatible donor. Methods for preparing hemogenic endothelial cells are known in the art, and include generation from human pluripotent stem cells. See, WO 2017/096215 and US 2019/0119643, which are hereby incorporated by reference in their entireties. See also, Ditadi et al., *Nature Cell Biol.* 17(5) 580-591 (2015); Sugimura et al., *Nature* 2017; 545(7655):432-438; Nakajima-Takagi et al, *Blood.* 2013; 121(3):447-458; Zambidis et al., *Blood.* 2008 Nov. 1; 112(9):3601-14 and Park et al, *Cytometry A.* 2013 January; 83(1): 114-126 (human embryoid body (hEB)-based hemato-endothelial differentiation methods for efficient hiPSC differentiation); Choi et al., *Cell Rep.* 2012 Sep. 27; 2(3): 553-567 (hPSC differentiation in coculture with OP9); Sandler et al, 2014 Jul. 17; 511 (17509):312-318 (endothelial cells to hematopoietic cells); see also Sluvkin, *Blood* 2013 122:4035-4046. In some embodiments, the number of HE cells to initiate the production of HSCs is at least about $10^6$ cells, about $10^7$ cells, or at least $10^8$ cells. In some embodiments, the hematopoietic stem cells produced according to this disclosure comprise long term hematopoietic stem cells (LT-HSCs), which exhibit superior engraftment, and reconstitute to functional, multi-lineage adult blood in the recipient. In some embodiments, HSCs include Lin−/Sca1+/c-kit+ cells.

In various embodiments, a pharmaceutical composition for cellular therapy is prepared that comprises a population of HSCs prepared by the methods described herein, and a pharmaceutically acceptable vehicle. The pharmaceutical composition may comprise at least about $10^2$ HSCs, or at least about $10^3$ HSCs, or at least about $10^4$ HSCs, or at least about $10^5$ HSCs, or at least about $10^6$ HSCs, or at least about $10^7$ HSCs, or at least $10^8$ HSCs. For example, in some embodiments, the pharmaceutical composition is administered, comprising from about 100,000 to about 400,000 (CD34+) HSCs per kilogram (e.g., about 200,000 cells/kg) of a recipient's body weight.

The HSCs for therapy or transplantation can be generated in some embodiments in a relatively short period of time, such as less than two months, or less than one month, or less than about two weeks, or less than about one week, or less than about 6 days, or less than about 5 days, or less than about 4 days, or less than about 3 days. In some embodiments, the endothelial cells are cultured with increased Dnmt3b and/or Gimap6 activity or expression for 1 to 4 weeks.

The cell composition may further comprise a pharmaceutically acceptable carrier or vehicle suitable for intravenous infusion or other administration route, and may include a suitable cryoprotectant. An exemplary carrier is DMSO (e.g., about 10% DMSO). Cell compositions may be provided in unit vials or bags, and stored frozen until use. In certain embodiments, the volume of the composition is from about one fluid ounce to one pint.

HSCs generated using the methods described herein are administered to a subject (a recipient), e.g., by intravenous infusion or intra-bone marrow transplantation. The methods can be performed following myeloablative, non-myeloablative, or immunotoxin-based (e.g. anti-c-Kit, anti-CD45, etc.) conditioning regimes.

The methods described herein can be used to generate populations of HSC for use in transplantation protocols, e.g., to treat blood (malignant and non-malignant), bone marrow, metabolic, and immune diseases. In some embodiments, the HSC populations are derived from autologous cells or universally-compatible donor cells or HLA-modified or HLA null cells. That is, HSC populations are generated from HE cells, the HE cells derived from developmentally plastic endothelial cells or iPSCs that were prepared from cells of the recipient subject or prepared from donor cells (e.g., universal donor cells, HLA-matched cells, HLA-modified cells, or HLA-null cells). In some embodiments, autologous-derived cells are used, and the recipient subject has a condition selected from multiple myeloma; non-Hodgkin lymphoma; Hodgkin disease; acute myeloid leukemia; neuroblastoma; Germ cell tumors; autoimmune disorders (systemic lupus erythematosus (SLE), systemic sclerosis); myelodysplastic syndrome, amyloidosis; or other condition treatable using an autologous HSC transplant. In some embodiments, autologous-derived cells (e.g., HSC are generated from cells from the recipient subject) are used, and the recipient subject does not have a hematological malignancy.

In some embodiments, the recipient subject has a condition selected from Acute myeloid leukemia; Acute lymphoblastic leukemia; Chronic myeloid leukemia; Chronic lymphocytic leukemia; Myeloproliferative disorders; Myelodysplastic syndromes; Multiple myeloma; Non- Hodgkin lymphoma; Hodgkin disease; Aplastic anemia; Pure red-cell aplasia; Paroxysmal nocturnal hemoglobinuria; Fanconi anemia; Thalassemia major; Sickle cell anemia; Severe combined immunodeficiency (SCID); Wiskott-Aldrich syndrome; Hemophagocytic lymphohistiocytosis; Inborn errors of metabolism; Epidermolysis bullosa; Severe congenital neutropenia; Shwachman-Diamond syndrome; Diamond-Blackfan anemia; and Leukocyte adhesion deficiency. In some such embodiments, allogeneic-derived or universally-compatible donor cells or HLA-modified or HLA-null cells are used for generating the HE cells. For example, HSC are generated from cells from a donor subject, that is, a subject other than the recipient subject. In some embodiments, the donor subject is matched with the recipient subject based on blood type and Human leukocyte antigen (HLA) typing).

As used herein, the term "about" means ±10% of the associated numerical value.

These and other aspects of the invention will now be described with the following non-limiting Examples.

EXAMPLES

During definitive hematopoiesis, the first set of HSCs are born from hemogenic endothelial cells in the AGM during fetal development. Therefore, endothelial and/or hemogenic endothelial cells could be a source for developing or expanding HSCs for clinical use provided the establishment of a repertoire of intrinsic and extrinsic factors that exist in the AGM microenvironment.

Induction of seven transcription factors (ERG, HOXA5, HOXA9, HOXA10, LCOR, RUNX1, and SPI1), as well as inhibition of TGFβ and CXCR7 or activation of BMP and CXCR4, enhance the human endothelial-to-HSPC transition. However, these approaches do not endow endothelial or hemogenic endothelial cells with LT-HSC function and properties. Blood flow-mediated shear stress with subsequent activation of NOS is the only known biomechanical factor responsible for HSC formation. However, cdh5-MO embryos produce HSCs despite a defect in blood flow, and L-NAME mediated NOS inhibition. Therefore, it is critical to identify biomechanical forces, mechanosensitive pathways, and epigenetic mechanisms that not only cross-talk in regulating HSC formation, but also have utility in developing long-term (LT), self-renewing HSCs.

Heartbeat precedes and triggers circulation by generating pulsation in blood vessels. However, the direct role of heartbeat-mediated biomechanical forces in HSC formation, in the absence of circulation, from the aortic endothelial lining of blood vessels remains unknown. Pulsation causes the biomechanical stretching of blood vessels and activates mechanosensitive receptors, such as transient receptor potential (TRP) channels, Piezo channels, Degenerin/Epithelial Sodium Channels (DEG/ENaC), and K1-family members. However, it is unknown if pulsation or mechanosensitive receptor activation could stimulate HSC formation. Even though Lis et al. (Lis R, et al. *Conversion of adult endothelium to immunocompetent haematopoietic stem cells Nature* 2017) and Sugimura et al. (Sugimura et al. *Haematopoietic stem and progenitor cells from human pluripotent stem cells Nature* 2017) demonstrated a method to convert human hemogenic endothelial cells to HSPCs, it is unknown which mechanisms could permanently erase their endothelial epigenetic landscape to become LT-HSCs.

As disclosed herein, the present disclosure demonstrates how heartbeat and/or pulsation-mediated biomechanical stretching and/or pharmacological activation of the Piezo1 mechanosensitive pathway enhances Dnmt3b expression, thereby erasing the endothelial epigenetic landscape to form HSCs (e.g., LT-HSCs). Furthermore, a bioreactor was developed that mimics pulsation-like conditions and established Piezo1 as a pharmacological target to stimulate and scale-up LT-HSC formation.

Heartbeat-Mediated Pulsation Stimulates the Endothelial-to-HSC Transition.

An unbiased zebrafish ethylnitrosourea (ENU) mutagenesis screen yielded malbec (bw209$^{mb}$), a zebrafish mutant for cadherin-5 (cdh5, ve-cdh). malbec and cdh5-morphant (MO) embryos display normal primitive and definitive hematopoiesis despite circulatory defects.

To identify blood flow and shear stress-independent biomechanical forces that stimulate the endothelial-to-HSC transition, the function and anatomy of the heart was analyzed as well as blood vessels in cdh5-deficient embryos.

Microangiography was first performed by injecting fluorescent dextran beads in the atrium of the two-chamber heart of the zebrafish embryo, and the dextran beads were then tracked in circulation. While the fluorescent dextran beads passed through the atrioventricular (AV) valve and the ventricle to enter general circulation in control embryos, they were trapped in the atrium of cdh5-morphant embryos.

To examine the structure of the heart, hearts were isolated from the control and cdh5-silenced embryos and immunohistochemistry was performed for the endothelial lining (gfp) and cardio-myocytes (mf20). It was found that the atrium (A), atrioventricular (AV) valve, ventricle (V), and outflow tract (OT) were formed in cdh5-morphants, but the AV valve was elongated and distorted.

To investigate why circulation was impaired in the cdh5-silenced embryos, the vascular structure was analyzed, as well as the blood circulation, heart rate, cardiac output, and cardiac tamponade in the cdh5-silenced embryos.

The integrity of the endothelial lining was analyzed in mlb×kdr:dsRED embryos. It was found that the structure of both arteries and veins were intact in cdh5-deficient embryos.

The temporal development of the heart, heartbeat, blood vessels, blood circulation, and HSC formation are conserved in zebrafish, mouse, and man. During zebrafish development, the heart begins to beat around 23 hours post fertilization (hpf), the blood circulation begins at approximately 24-26 hpf, and definitive HSCs emerge from hemogenic endothelial cells in the AGM region between 30-48 hpf.

To analyze the circulation in blood vessels before and after the heart begins to beat, time-lapse confocal imaging was performed of the control and cdh5-silenced lcr:eGFP ×flk1:mCherry embryos.

It was found that lcr:eGFP$^+$ red blood cells were accumulated in the blood vessels of cdh5-silenced embryos even after the heart begins to beat; demonstrating the absence of active circulation in cdh5-morphants, despite the initiation of heartbeat and formation of blood vessels.

To examine the function of the heart in the cdh5-silenced embryo, electrophysiology and echocardiography assessments were performed. The heart rate in the cdh5-MO embryos was comparable to the control, but stroke volume was near null in cdh5-MO embryos. Therefore, it was established that cardiac output (=stroke volume×heart rate) was impaired in cdh5-MO embryos.

The cdh5-MO embryos had pericardial edema in the cardiac cavities, which may be due to the back-flow of blood from the heart. The accumulation of fluid in the pericardial space results in a reduced ventricular filling and a subsequent hemodynamic compromise. To examine whether cardiac tamponade was a factor in the accumulation of fluid in the pericardial space, the cardiac cavity of cdh5-MO embryos were punctured, like in pericardiocentesis, and then pericardial fluid was aspirated to reduce the fluid-pressure buildup on the heart. However, the cardiac output deficiency of the cdh5-morphant heart could not be rescued.

Heartbeat was normal in cdh5-morphants, but their cardiac output was impaired due to structural defects in the heart, resulting in the accumulation of blood in the pericardial cavity. Since cdh5-MO embryos have normal hematopoiesis, it was hypothesized that the heartbeat-derived biomechanical forces influence HSC formation in the absence of active circulation.

Although cdh5-MO embryos have beating hearts and no active circulation, they have HSCs forming in the aortic endothelium of their blood vessels. When the AGM of control zebrafish embryos were zoomed in on, a distinct pulsation of the blood vessels was noticed. To distinguish the existence of pulsation in blood vessels independent of circulating blood cells and perhaps blood flow, the pulsation frequency of blood vessels with that of the circulating blood cells and movement due to the blood flow was compared. Specifically, the time-lapse confocal imaging of a double transgenic line with circulating lcr:eGFP$^+$ red cells within flk1:mCherry$^+$ blood vessels, as well as Fourier analysis of the signal from both blood vessels and from the circulating blood cells was performed. The frequency spectrum of blood vessels was found to have a distinct peak. Thus, the pulsation in blood vessels and the blood flow co-exist, but their existence and nature are independent of each other.

To investigate the temporal, spatial, and functional existence of pulsation in the AGM at 36 hpf, the light sheet microscopy of the blood vessels region in control zebrafish embryos followed by Fourier analysis was performed. The data further corroborate that the AGM has a distinct pulsation frequency at 36 hpf; which is the time and location for the endothelial-to-hematopoietic transition as seen with time-lapse confocal imaging of runx1:mCherry$^+$ HSPCs emerging from flk1:eGFP$^+$ endothelial cells. Together, the AGM region is found to be pulsating and the pulsation in the AGM is concurrent with the endothelial-to-hematopoietic transition.

Blood vessels are under constant mechanical loading from heartbeat-mediated blood pressure and flow, which cause circumferential wall stress and endothelial shear stress. While blood flow imposes shear stress on endothelial cells and induces vasodilation, heartbeat-mediated pulsation generates circumferential stretch and causes mechanical distension on both endothelial cells and smooth muscle cells.

To analyze if cdh5-MO embryos form HSCs through or are independent of blood flow- and shear-stress mediated NOS activation, HSPC expression was analyzed in control and cdh5-MO embryos treated with L-NAME, a NOS inhibitor. It was demonstrated that the inhibition of NOS attenuates HSPC formation in control embryos, but it does not impact HSPC formation in cdh5-MO embryos. Therefore, cdh5-MO embryos form HSCs independent of NOS activation.

Taken altogether, heartbeat-mediated pulsation stimulates the endothelial-to-HSC formation independent of circulation.

Stretch Activates Piezo1 for HSC Formation.

Since biomechanical forces stimulate cell shape and fate transitions, it was hypothesized that the pulsation-mediated periodical stretching of the hemogenic endothelium stimulates HSC formation.

Figure 2A:
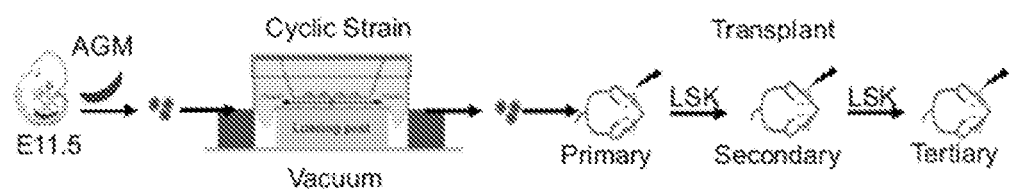
FIG. 2A shows an experimental outline (top) and a line graph (bottom). The experimental outline (top) shows a schema representing serial transplantations of HSCs originating in E11.5 mouse AGM followed by treatment with 10% cyclic strain or Yoda1 into myeloablative immunocompromised mice. The line graph (bottom) shows the percentage peripheral blood chimerism from reconstitution of E11.5 AGM (donor; three embryo equivalent)-derived HSCs in a primary transplant (recipient) at four-week intervals between weeks 8-16; indicating that cyclic strain or pharmacological activation of Piezo1 (Yoda1 treatment) to E11.5 AGM stimulates the formation of HSCs. n≥5 primary recipients per group. *P<0.05 vs. control; $P<0.05 vs. week 8 chimerism. Three embryo equivalent (e.e.) AGM donor cells were injected in each recipient.
Figure 2A:
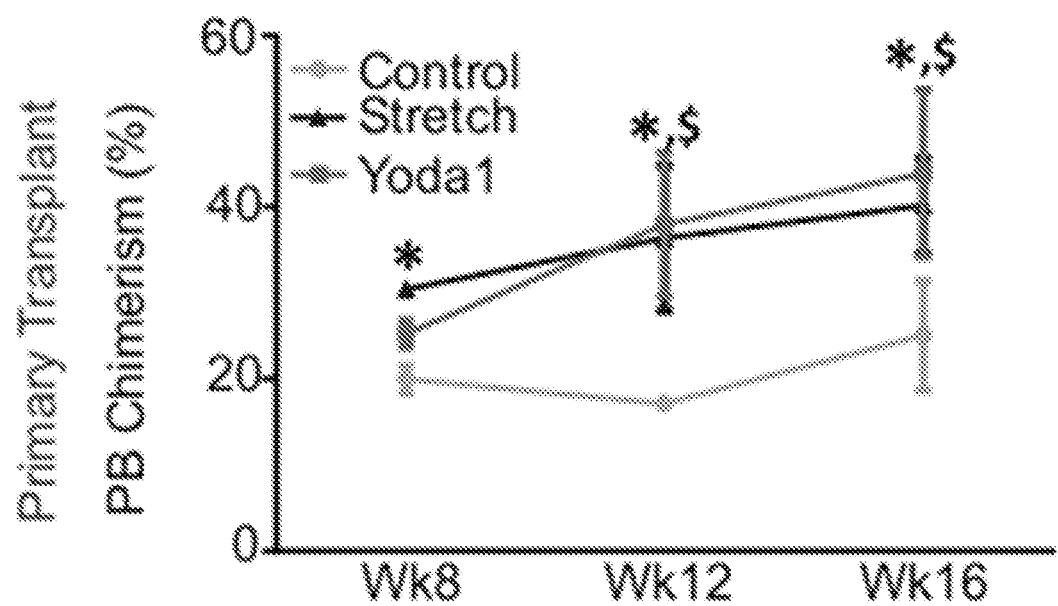

To test the function of pulsation in endothelial-to-HSC formation, a bioreactor was developed that could apply cyclic strain on AGM cells harvested from E11.5 mice embryos (FIG. 2A, top panel). Hematopoietic colony formation and flow analyses assays demonstrated that 10% cyclic strain potentiates the formation of multipotent hematopoietic progenitors, which is attenuated by GdCl$_3$-mediated pan-pharmacological inhibition of stretch-activated receptors (SAR). GdCl$_3$ also attenuated HSPC expression in zebrafish embryos to the level of sih-MO embryos.

The SAR family members have four sub-categories: K1-family members as well as Piezo, TRP, and DEG/ENaC channels. Tissue expression and computational analyses display Piezo1 and Trpv4 in endothelial and hematopoietic tissues, so their roles were tested in the endothelial-to-HSC transition.

The loss-of-function analyses and pharmacological inhibition of trpv4 and piezo1 abolished HSPC marker expression and the endothelial-to-HSC transition (FIG. 1A). Conversely, pharmacological activation of trpv4 or piezo1 enhanced HSPC marker expression in control embryos, and rescued HSPC expression in sih-embryos. Upon temporal and spatial analyses, trpv4 was not detected in the AGM region of zebrafish embryos at 36 hpf, whereas Piezo1 co-localized with Cd31 (endothelial) and c-Kit (hematopoietic) in E11.5 AGM.

To consolidate the molecular mechanism underlying stretch-mediated HSC formation, whole transcriptome analyses of AGMs treated with either cyclic strain or a pharmacological activator of Piezo1 was performed. It was found that cyclic strain and Piezo1 activation produced similar gene signatures (FIG. 1).

Figure 1D:
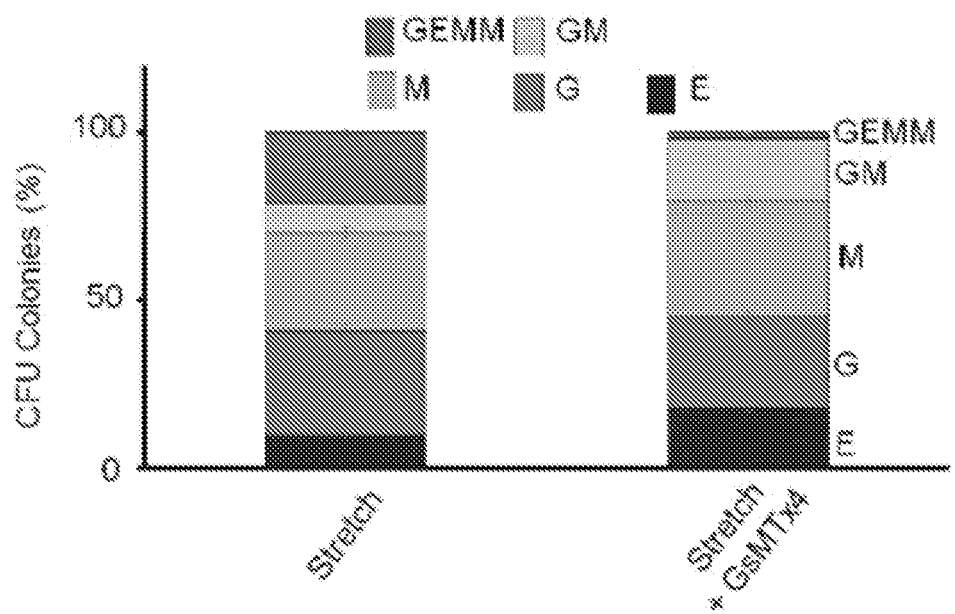
FIG. 1D shows a graph of hematopoietic CFU assays on E11.5 AGM cells, which demonstrate that GsMtX4-mediated pharmacological inhibition of Piezo1 attenuates the inductive impact of cyclic strain on the endothelial-to-HSC transition. n≥6 per group. *P<0.05 vs. Control. Abbreviations: GEMM (granulocyte, erythroid, macrophage, megakaryocyte); GM (granulocyte macrophage); G (granulocyte); M (macrophage); E (erythroid).

The pharmacological activation of Piezo1 further enhanced multipotent hematopoietic progenitor cell formation (FIG. 1C), whereas the pharmacological inhibition of Piezo1 attenuated the cyclic strain-mediated induction of HSPC formation (FIG. 1D). Together, cyclic strain-mediated biomechanical stretching activates Piezo1 to stimulate the endothelial-to-HSC transition.

Biomechanical Stretching or Piezo1 Activation Produces LT-HSCs.

Figure 2B:
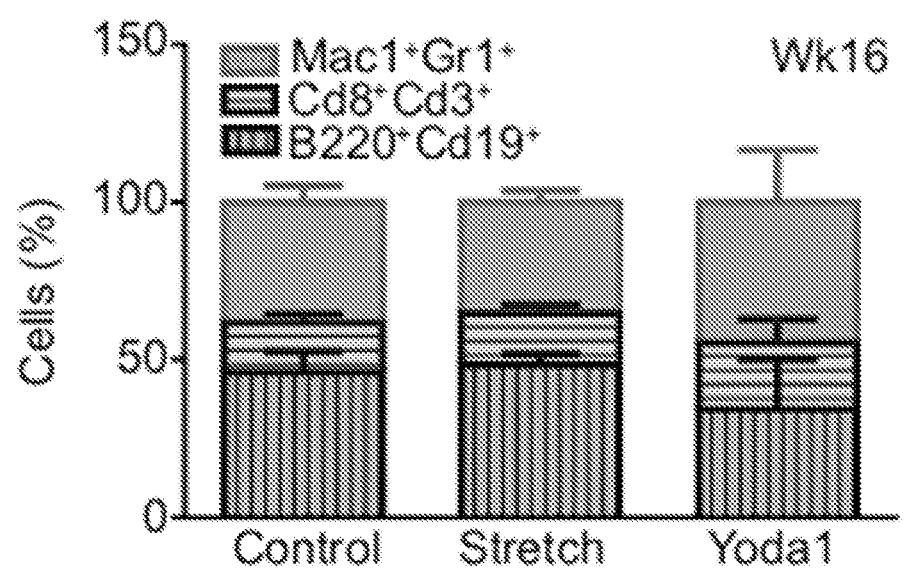
FIG. 2B is a graph showing the percentage reconstitution of E11.5 AGM (donor; three embryo equivalent)-derived HSCs to Mac1+Gr1+ myeloid cells, Cd8+Cd3+ T-cells, and B220+Cd19+ B-cells in a primary transplant (recipient) at week 16; indicating that cyclic strain or pharmacological activation of Piezo1 (Yoda1) to E11.5 AGM stimulates the formation of HSCs that reconstitute to the blood. n≥5 primary recipients per group.
Figure 2C:
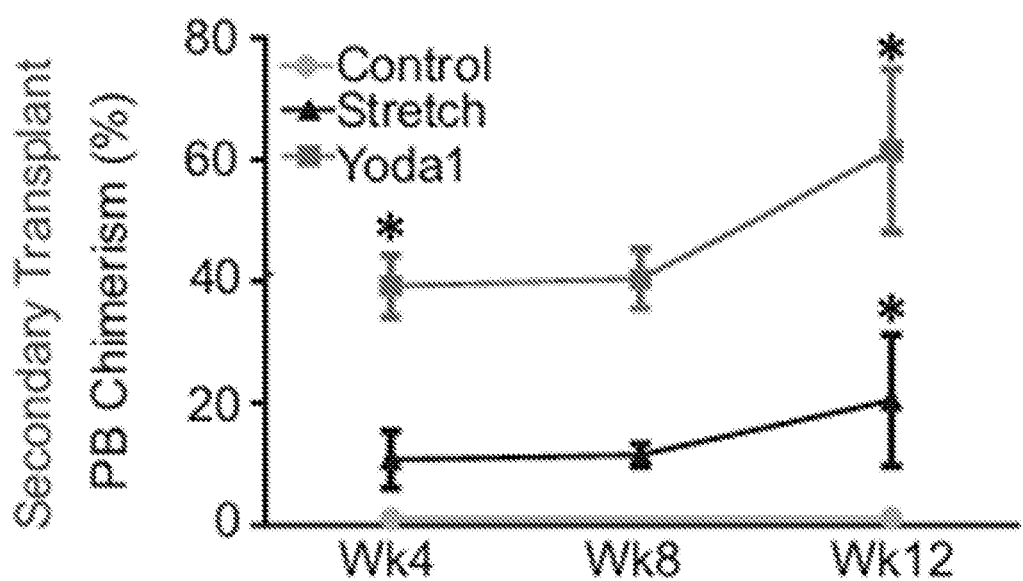
FIG. 2C is a line graph showing the percentage peripheral blood chimerism from reconstitution of primary transplant (donor)-derived flow-sorted Lin−Sca1+c-Kit+ HSPCs (n=2000) in a secondary transplant (recipient) at four-week intervals between weeks 8-12; indicating that cyclic strain or Yoda1 treatment of E11.5 AGM produces HSCs that have serial engraftment and self-renewal capacities. n≥5 secondary recipients per group. *P<0.05 vs. control.
Figure 2D:
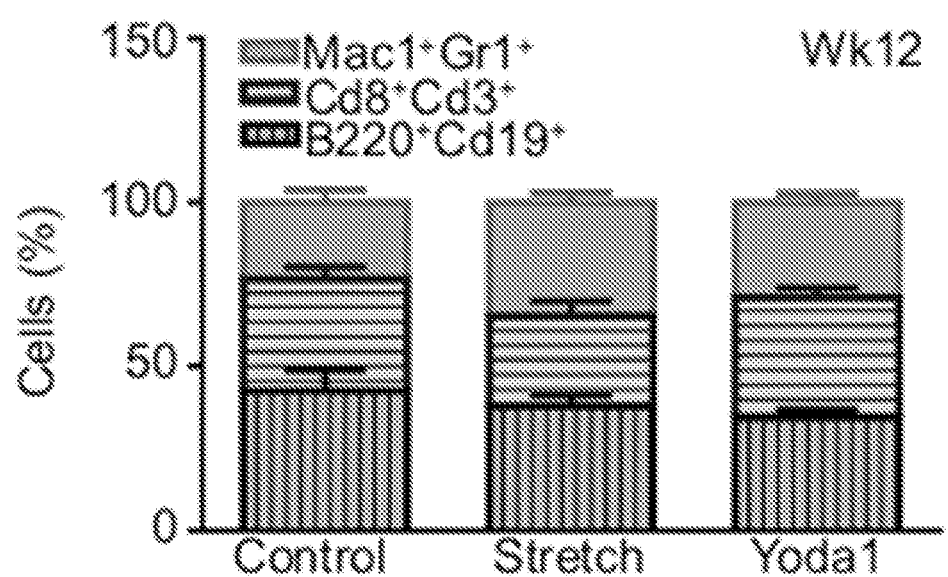
FIG. 2D is a graph showing the percentage reconstitution of primary transplant (donor)-derived HSCs to Mac1+Gr1+ myeloid cells, Cd8+Cd3+ T-cells, and B220+Cd19+ B-cells in a secondary transplant (recipient) at week 12; indicating that cyclic strain or Yoda1 treatment of E11.5 AGM produces HSCs that can serially reconstitute to the blood. n≥5 secondary recipients per group.

To analyze if cyclic strain or Piezo1 activation produces long-term, self-renewing HSCs (LT-HSCs), serial transplantation assays were performed. The primary transplant of cyclic strain or Piezo1 activator treated AGMs displayed higher engraftment and normal multi-lineage reconstitution (FIG. 2A, FIG. 2B). Also, the bone marrow of primary recipients transplanted with cyclic strain or Piezo1 activator treated AGMs displayed two- to three-times higher amount of Lin$^-$Sca1$^+$c-Kit$^+$Cd48$^-$Cd150$^+$ HSCs. The transplantation of primary recipient-derived sorted Lin$^-$Sca1$^+$c-Kit$^+$ HSPCs into immunocompromised secondary recipients also resulted in higher engraftment and normal multi-lineage reconstitution (FIG. 2C, FIG. 2D). Therefore, it was predicted that both cyclic strain and/or Piezo1 activation produce higher amounts of normal LT-HSCs. To test this hypothesis, a limiting dilution assay was performed by transplanting graded amount of Lin$^-$Sca1$^+$c-Kit$^+$ HSPCs into immunocompromised tertiary recipients. The tertiary transplant analyses demonstrated that cyclic-strain produced two- to three-times higher amount of LT-HSCs.

Figure 3A:
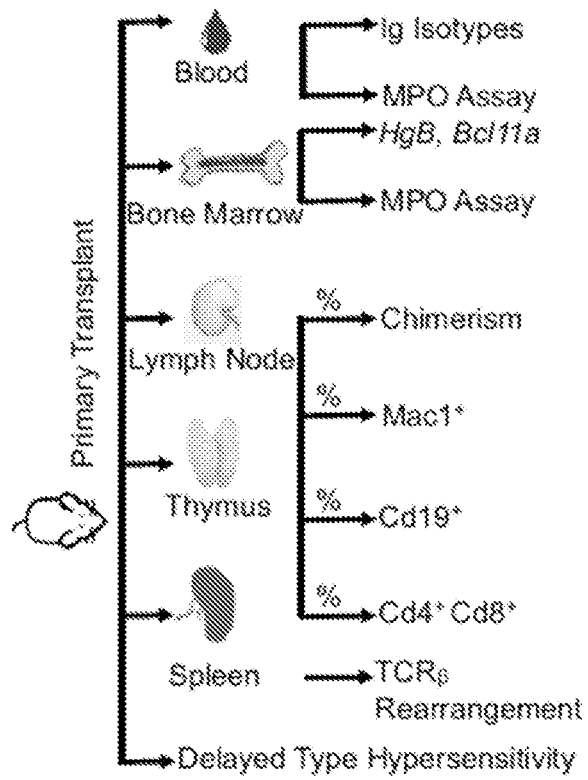
FIG. 3A shows an experimental outline (top) and a graph (bottom). The experimental outline (top) shows strategies for functional and phenotypic analyses of donor-derived blood lineages in hematopoietic tissues of primary transplant (recipient mice). The graph (bottom) shows the percentage expression of β-major (adult), εγ (embryonic), and β-H1 (embryonic) types of hemoglobin in bone marrow-derived Cd71+Ter119+ sorted (donor) erythroid cells; the data indicates that donor HSCs produced following biomechanical stretching or Yoda1-treatment of E11.5 AGM reconstitutes to red cells containing adult hemoglobin. n≥6 per group.
Figure 3A:
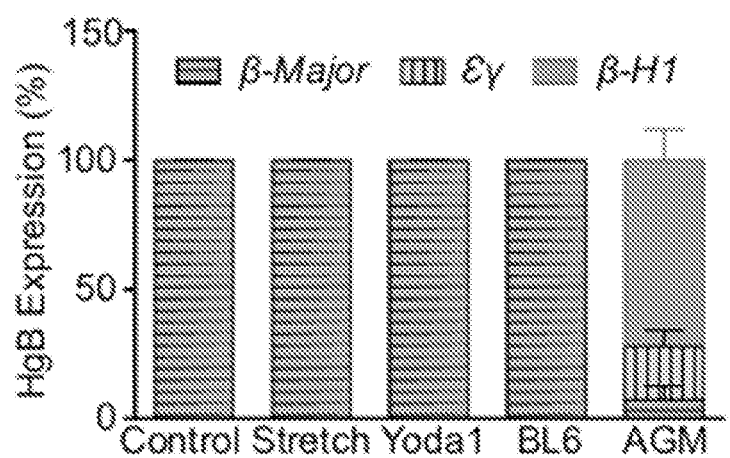
Figure 3B:
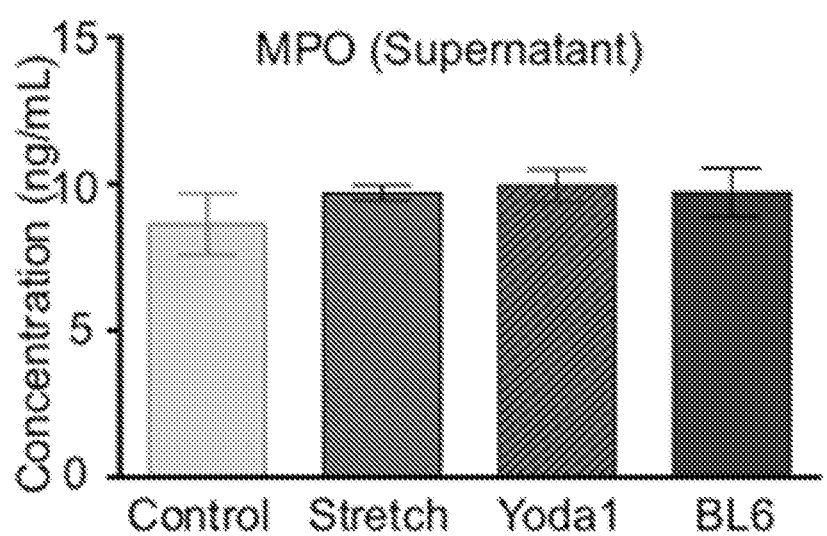
FIG. 3B is a graph showing an overnight culture (O/N) of bone marrow-derived Gr1+Mac1+ sorted (donor) neutrophils followed by ELISA-based quantification of myeloperoxidase (MPO) proteins; the data demonstrate that donor HSCs were produced following biomechanical stretching or Yoda1 treatment of E11.5 AGM, which reconstitute to functional myeloid cells displaying sufficient MPO levels. n≥5 per group.
Figure 3C:
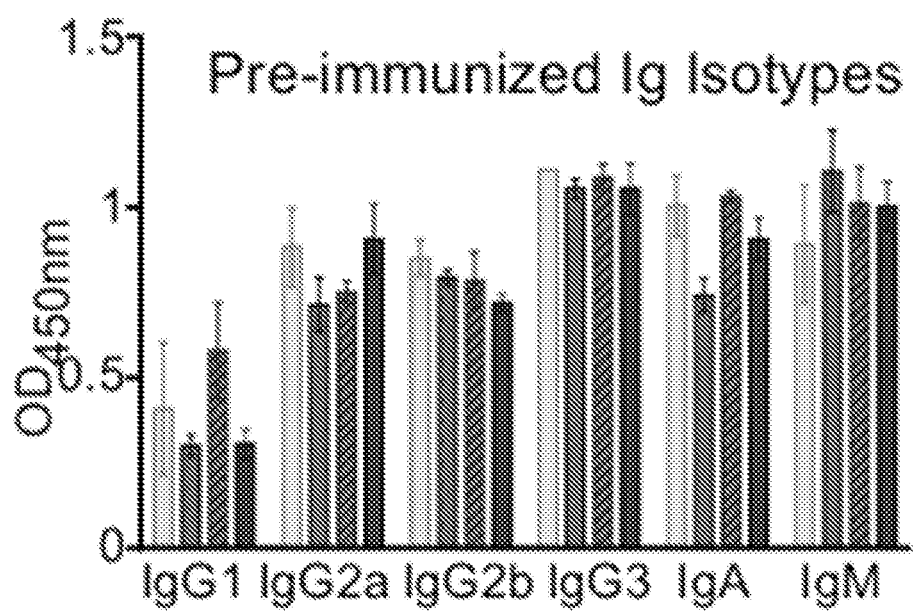
FIG. 3C is a graph showing ELISA analyses of pre-immunized immunoglobulin (Ig) isotypes in the peripheral blood of primary transplant (recipient) mice; the data indicates that primary transplant produces B-cells with a complete repertoire of immunoglobulins. n≥6 per group.
Figure 3D:
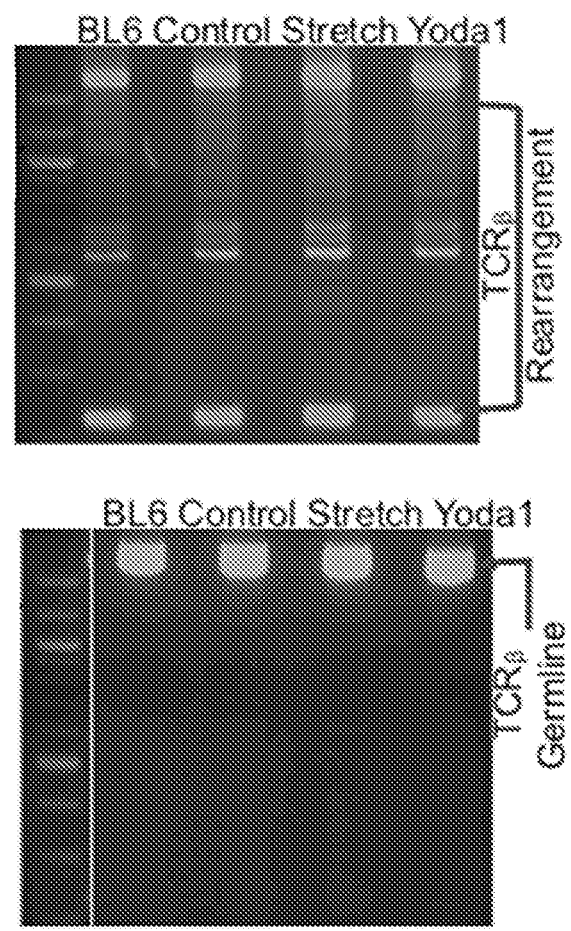
FIG. 3D is an image of two gel pictures showing T-cell receptor (TCR$^β$) locus analyses of spleen-sorted Cd3+ T cells (donor) (top) or Mac1+ myeloid cells (donor; negative control) (bottom); the data indicates that donor HSCs produced T-cells and display T-cell receptor β (TCR β) rearrangement following biomechanical stretching or Yoda1-treatment of E11.5 AGM, which migrate to the spleen and reconstitute to T-cells that possess functional recombination machinery sufficient to rearrange TCR$_β$ locus.
Figure 3E:
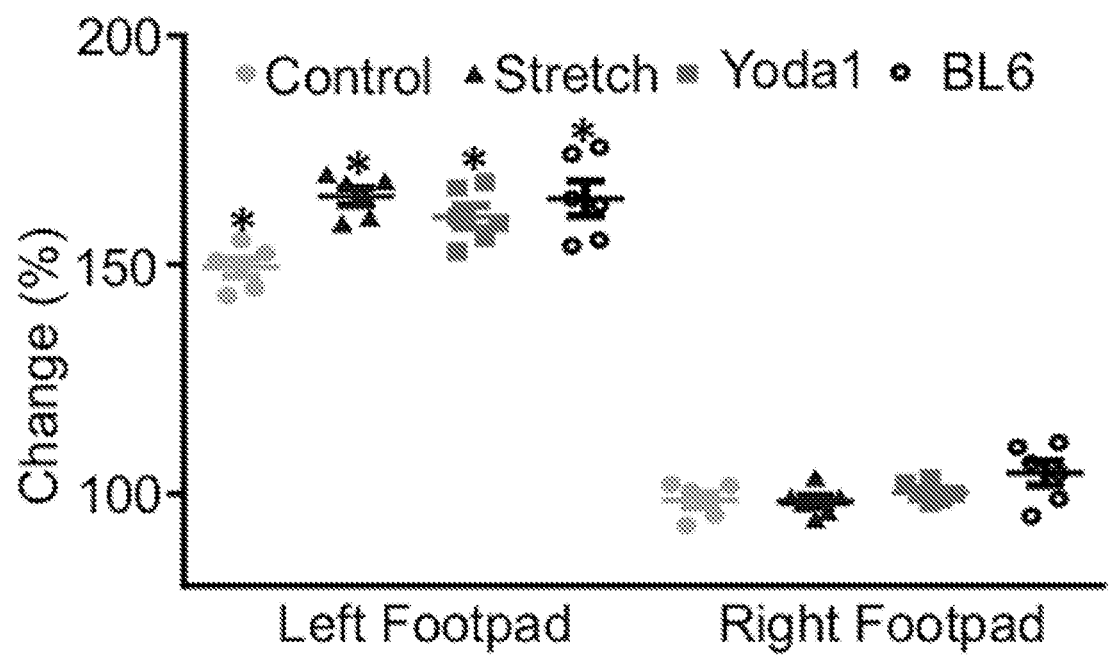
FIG. 3E is a dot plot showing delayed-type hypersensitivity assay, which demonstrates that primary transplant (recipient) mice reconstituted with biomechanical stretching or Yoda1-treated E11.5 AGM-derived donor HSCs possess T-cell mediated immune response. n≥6 per group. *P<0.05 vs. right footpad (negative control).

To investigate if AGM-HSCs (donor) engraft and reconstitute to adult normal blood, the molecular features and functional properties of reconstituted blood lineages were then analyzed in the primary recipients transplanted with control, cyclic strain or Piezo1 activator treated AGMs. The analysis of donor-derived erythroid cells in the bone marrow displayed Cd71$^+$/Ter119$^+$ expression, as well as enhanced expression of adult globin markers at the cost of embryonic globin in the presence of Bcl11a (FIG. 3A). Further analysis of donor-derived myeloid cells in the bone marrow and blood serum displayed sufficient amounts of Gr1$^+$/Mac1$^+$ myeloid cells, as well as their production of myeloperoxidase (MPO) (FIG. 3B). Next, analyses of donor-derived chimerism, Mac1$^+$ myeloid cells, Cd19$^+$ B-cells, as well as Cd4$^+$/Cd8$^+$ T-cells in the lymph node, thymus, and spleen demonstrated that donor HSC-derived progenitors circulated and colonized in the hematopoietic niches to reconstitute to adult blood lineage. Upon analyses of primary transplant-derived blood serum, it was also found that they produced the normal repertoire of pre-immunized immunoglobulins (Ig), such as IgG1, IgG2a, IgG2b, IgA, and IgM (FIG. 3C). The sorting of donor-derived Cd3$^+$ T-cells from the spleen demonstrated T-cell receptor β (TCR β) rearrangement, which was absent in donor-derived Mac1$^+$ myeloid cells (negative control) from the spleen (FIG. 3D). To analyze the functional properties of T-cells in primary transplant, the delayed-type hypersensitivity assay demonstrated the successful recruitment of antigen-specific functional T-cells in footpad, by sensitizing primary transplant with sheep red blood cell injection (FIG. 3E). Thus, cyclic strain or Piezo1 activation of AGMs or hemogenic endothelial cells produced HSCs that engrafted in hematopoietic niches and reconstituted to functional, multi-lineage adult blood.

Biomechanical Stretching and Piezo1 Activation Upregulate Dnmt3b for the Endothelial-to-HSC Transition.

Figure 4:
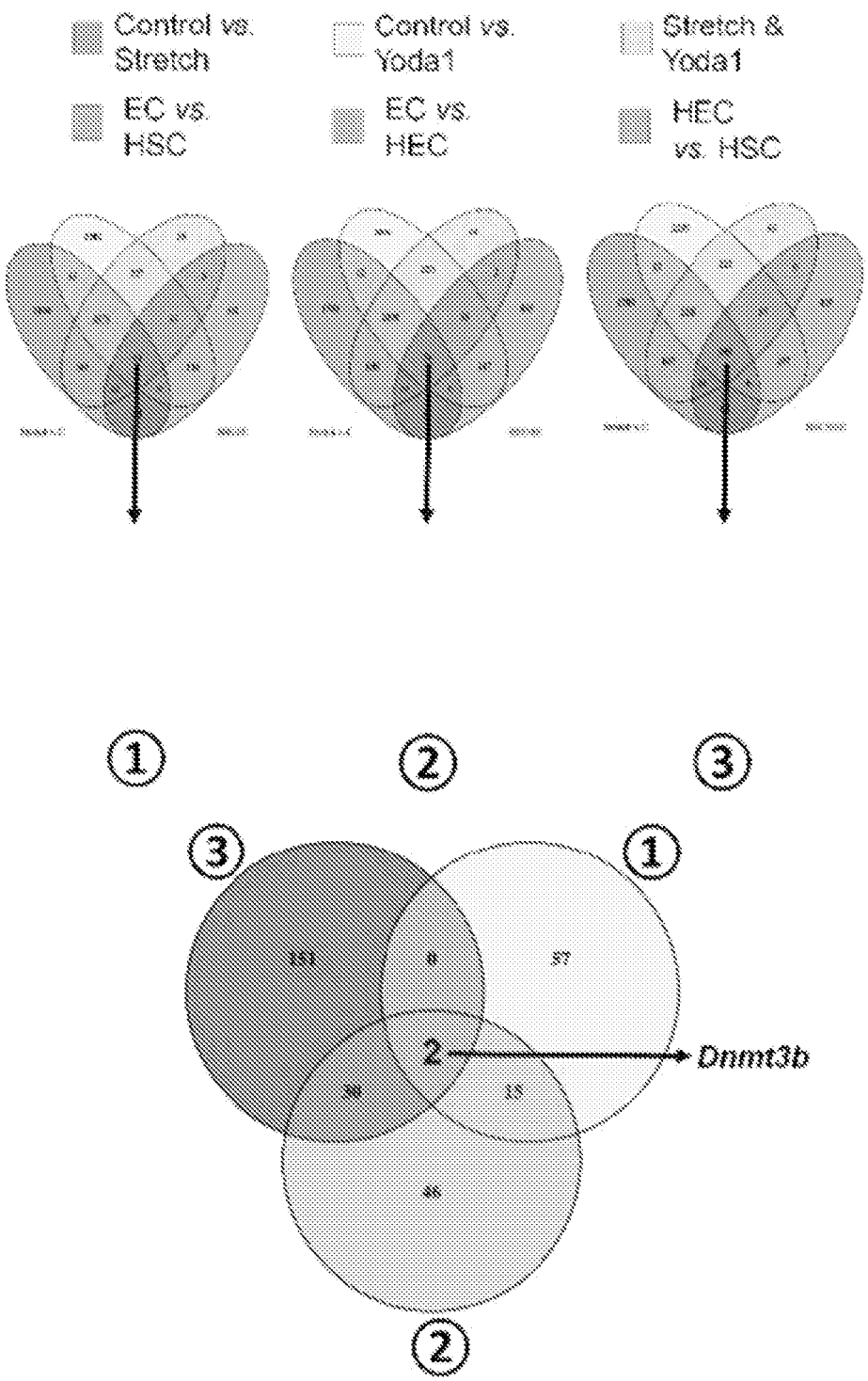
FIG. 4 shows Venn diagrams of genes up-regulated in E11.5 AGM cells treated with cyclic strain and/or Yoda1 in the context of genes up-regulated during EC vs. HSC (①), EC vs. HEC (②), and HEC vs. HSC (③). The Venn comparison of the commonly upregulated genes in the above analyses (① vs. ② vs. ③) demonstrates that both circumferential stretching and Piezo1 activation specifically stimulate Dnmt3b transcript expression and Gimap6 transcript expression during the endothelial-to-HSC transition.

Since the AGM is a heterogeneous tissue, it was unclear how stretch-mediated Piezo1 activation would stimulate the aortic endothelial cell fate transition to HSCs. Differential gene expression signatures from E10.5 AGM-sorted endothelial cells, hemogenic endothelial cells, and HSCs were developed. Hierarchical clustering of gene signatures derived upon cyclic strain or Piezo1 activation of the AGM in the context of AGM-derived endothelial cells, hemogenic endothelial cells, and HSCs further provided the quantitative overview of overexpressed biological processes, molecular pathways, gene expression clusters, and their gene ontology (GO) terms. Venn diagram analyses of cyclic stretch and/or Piezo1 activation-mediated genes upregulated during the endothelial-to-HSC transition identified Dnmt3b as a potential candidate mechanism responsible for the silencing of endothelial machinery required for HSC formation (FIG. 4). In addition, Gimap6 was also identified as a potential candidate mechanism responsible for the silencing of endothelial machinery required for HSC formation.

To validate the bioinformatics and computational analyses, the temporal and spatial protein expression of Dnmt3b in E11.5 AGM was analyzed. The immunohistochemistry assay demonstrated that Dnmt3b co-localizes with Cd31$^+$ endothelial and c-Kit$^+$ hematopoietic cells. Thus, it was hypothesized that Dnmt3b could stimulate the endothelial-to-HSC transition.

Figure 5A:
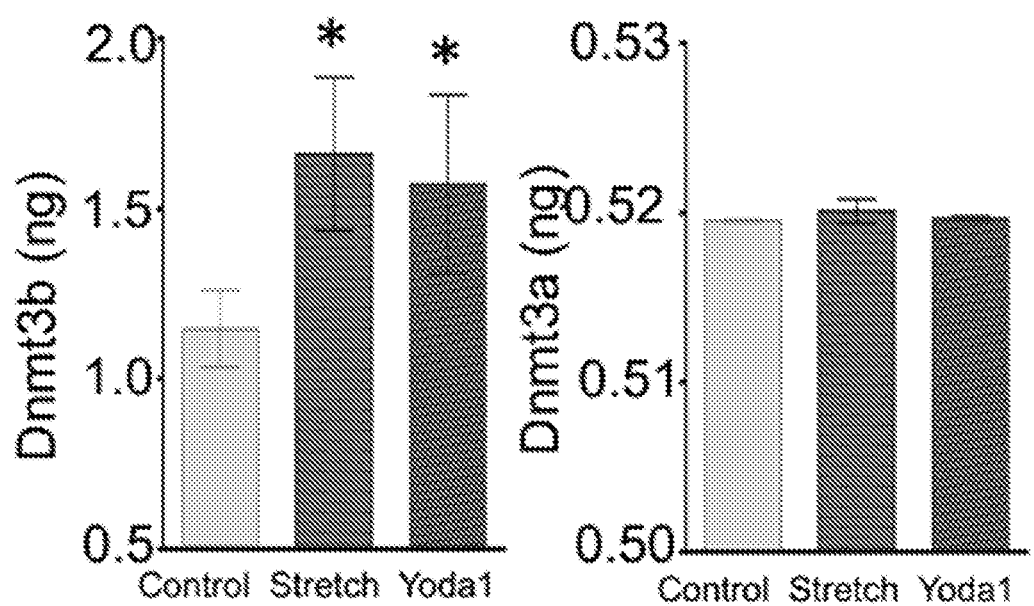
FIG. 5A shows two graphs of the protein levels of Dnmt3b and Dnmt3a in nuclear fractions of E11.5 mouse AGM cells treated with cyclic strain or Yoda1; the data demonstrates that circumferential stretching or Piezo1 activation specifically stimulates Dnmt3b protein expression levels without impacting the expression of Dnmt3a. n≥3 per group. *P<0.05 vs. Control.

Although Dnmt3b and Dnmt3a are highly homologous and have distinct functions in HSC maintenance or differentiation, their potential roles in the endothelial-to-HSC in AGM were unknown. The gene signatures and tissue expression analyses excluded any involvement of Dnmt3a in HSC formation in the AGM. To distinguish the distinct or overlapping hemogenic role(s) of Dnmt3b and Dnmt3a, Dnmt3b and Dnmt3a protein levels were analyzed in nuclear fractions of cyclic strain- or Yoda1-treated AGM cells, which established that cyclic strain or Piezo1 activation stimulates Dnmt3b protein expression, and not Dnmt3a, in E11.5 AGM cells (FIG. 5A).

To analyze whether the pulsation of blood vessels, in the absence of blood flow, stimulated HSC formation via Dnmt3b activation, HSPC marker expression was measured in cdh5-MO embryos treated with Nanaomycin, a Dnmt3b inhibitor. The pharmacological inhibition of Dnmt3b attenuated HSPC marker expression in control and cdh5-MO embryos.

Figure 5B:
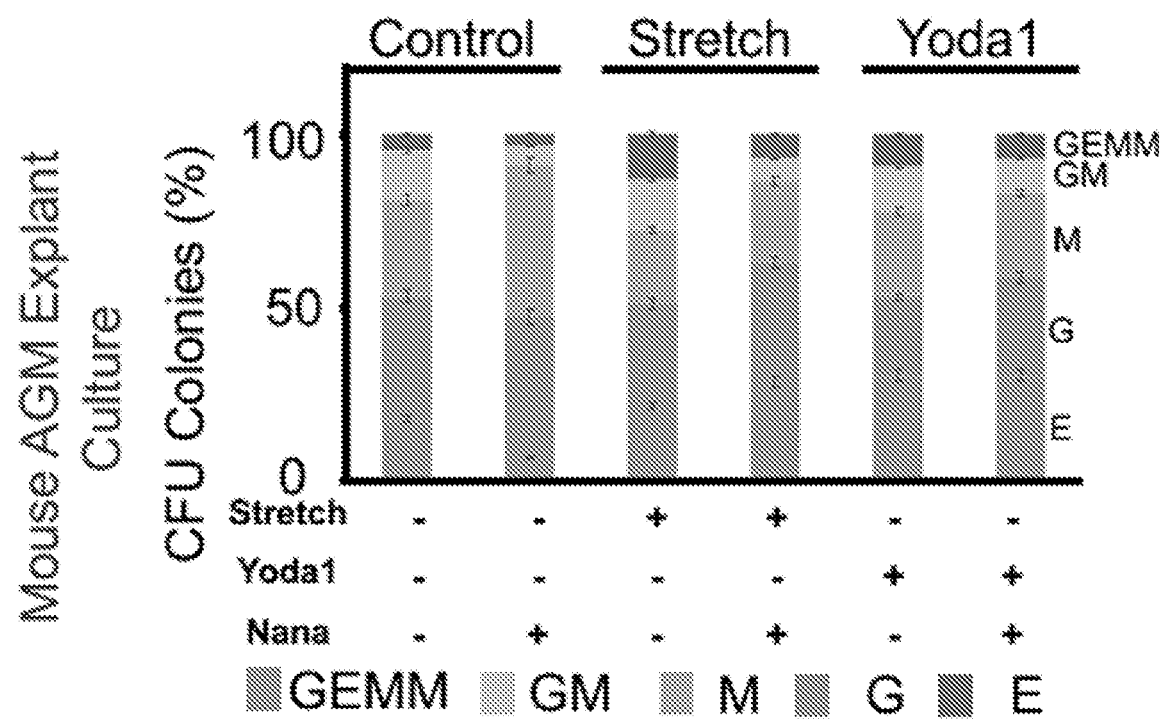
FIG. 5B shows a graph of the hematopoietic CFU assays of E11.5 mouse AGM cells treated with cyclic strain or Yoda1 in the presence of Nanaomycin (Nana); the data indicates that the pharmacological inhibition of Dnmt3b attenuates the endothelial-to-HSC transition stimulated by circumferential stretch or Piezo1 activation. n≥6 embryos per group. *P<0.05 vs. Control; $P<0.05 vs. Stretch; +P<0.05 vs. Yoda1.
Figure 5C:
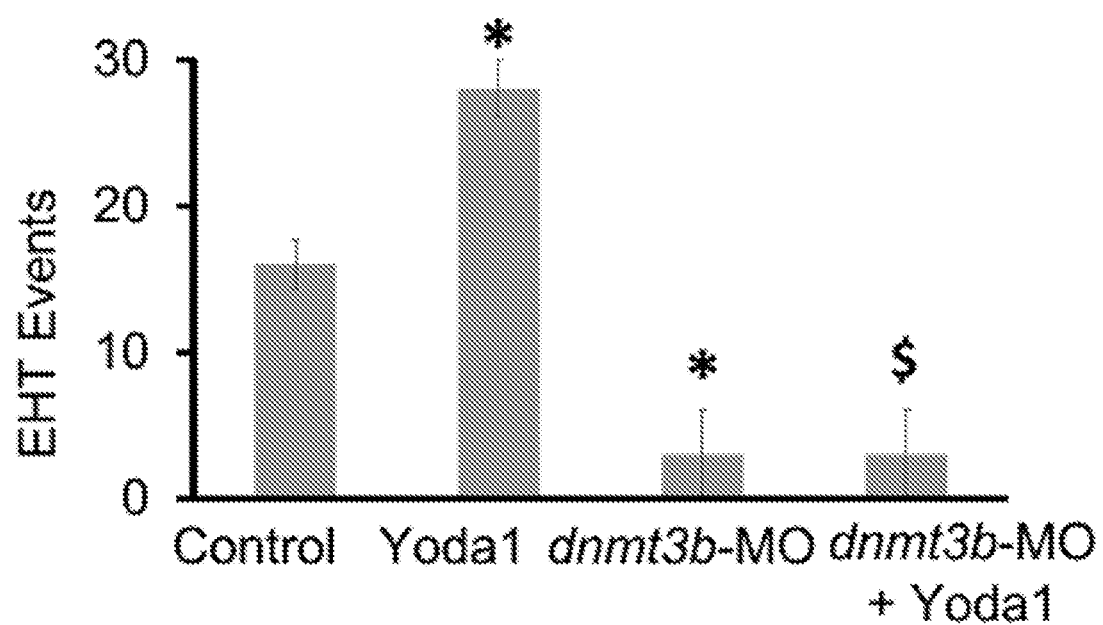
FIG. 5C is a graph showing the results of time-lapse confocal imaging of cd41:eGFP+ HSCs emerging from flk1:mCherry+ endothelial cells in transgenic embryos between 26-42 hpf; the data demonstrates that the silencing of dnmt3bb.1 attenuates the endothelial-to-HSC transition stimulated by piezo1 activation, and the specificity of Nanaomycin for Dnmt3b over Dnmt3a. n≥5 per group. *P<0.05 vs. control; $P<0.05 vs. Yoda1.

Next, the experiments of this example analyzed whether biomechanical stretching or Piezo1 activation stimulated the endothelial-to-hematopoietic transition via Dnmt3b activation. It was found that the inhibition of Dnmt3b attenuated the biomechanical stretching- or Piezo1 activation-mediated induction of multipotent hematopoietic progenitor cell formation (FIG. 5B), as well as the endothelial-to-hematopoietic transition (FIG. 5B). Although Nanaomycin treatment reverts hematopoietic cells into phenotypic endothelial cells, such endothelial cells were not functional. The whole mount in situ hybridization of HSPC markers, as well as time-lapse imaging of the endothelial-to-HSC transition in Nanaomycin-treated or dnmt3b-MO-injected zebrafish embryos concurrently treated with or without Yoda1 further validated that the inhibition or the loss of dnmt3b attenuated the Piezo1 activation-mediated increase in HSC formation (FIG. 5C). Together, pulsation-mediated Piezo1 activation enhanced Dnmt3b expression in the AGM to stimulate the endothelial-to-HSC transition.

Production of HSCs from HE Cells Generated from Human iPSCs

Embryoid body and hemogenic endothelium differentiation was performed as described in (Sugimura et al. 2017; Ditadi et al. 2015). Briefly, hiPSC colonies were dissociated with 0.05% trypsin for 5 min at 37° C., washed with PBS+2% FBS, and resuspended in StemPro-34 (Invitrogen, 10639-011) supplemented with L-glutamine (2 mM), penicillin/streptomycin (10 ng/ml), ascorbic acid (1 mM), human holo-Transferrin (150 g/ml, Sigma T0665), monothioglycerol (MTG, 0.4 mM), BMP4 (10 ng/ml), and Y-27632 (10 μM). Five million cells were seeded into 10 cm dishes (Ezsphere, Asahi Glass) for the spheroid formation. On Day 1, bFGF (5 ng/ml) and BMP4 (10 ng/ml) was added to the medium. On Day 2, the media was changed with the StemPro-34 supplemented with SB431542 (6 μM), CHIR99021 (3 μM), bFGF (5 ng/ml), and BMP4 (10 ng/ml). On Day 3, the medium was replaced with StemPro-34 supplemented with VEGF (15 ng/ml) and bFGF (10 ng/ml). On day 6, the medium was changed to StemPro-34 supplemented with bFGF (5 ng/ml), VEGF (15 ng/ml), interleukin (IL)-6 (10 ng/ml), IGF-1 (25 ng/ml), IL-11 (5 ng/ml), SCF (50 ng/ml) and EPO (2IU). The cells were maintained in a 5% $CO_2$, 5% $O_2$ and 95% humidity incubator. All cytokines were purchased from Peprotech.

To isolate the CD34$^+$cells, the embryoid bodies (from day 8) were dissociated by 0.05% trypsin, filtered through a 70 m strainer, CD34$^+$cells were isolated by CD34 magnetic bead staining, and subsequently passaged through the LS columns (Miltenyi). A sample from every batch was tested by FACS to validate its purity with the panel. The following antibodies were employed: CD34-PEcy7 (Clone 581; Biolegend), FLK1-PE (CLONE #89106; BD), and 4',6-diamidino-2-phenylindole (DAPI).

Isolated CD34$^+$cells were resuspended in StemPro-34 medium containing Y-27632 (10 μM), TPO (30 ng/ml), IL-3 (10 ng/ml), SCF (50 ng/ml), IL-6 (10 ng/ml), IL-11 (5 ng/ml), IGF-1 (25 ng/ml), VEGF (5 ng/ml), bFGF (5 ng/ml), BMP4 (10 ng/ml), and FLT3 (10 ng/ml) (Ferrel et al 2015). Cells were seeded at a density of 50,000 cells per well onto thin-layer Matrigel-coated 24-well plates. One day after seeding, Yoda1 (between 6.25 and 100 µM) was added to the cultures. After 7 days, the floating cells were collected and FACS analysis performed. For FACS analysis, cells were stained with CD34-PEcy7 (Clone 581; Biolegend) and CD45-APC (clone 2D1; Biolegend). All the cytokines were purchased from Peprotech.

Yoda1 induced the endothelial-to-hematopoietic transition in human iPSC-derived HE cells (data not shown). This effect was dose dependent.

CONCLUSIONS

The development, expansion, and maintenance of long-term HSCs have been a holy grail in stem cell biology and hematopoiesis. Based on time-lapse confocal, light sheet, and Fourier Transform analyses in zebrafish, not only was a scalable bioreactor simulating pulsation in blood vessels established, but also Piezo1 activation was identified as a pharmacological target to transform endothelial cells into LT-HSCs. This study provides a novel transgene-free approach to developing LT-HSCs that can engraft, self-renew, and reconstitute to multi-lineage, functional, adult blood upon serial transplantation.

Heartbeat-mediated pulsation generated circumferential stretch and caused mechanical distension on both endothelial cells and smooth muscle cells. However, Piezo1 was co-expressed between endothelial and hematopoietic cells in E11.5 AGM, but not in vascular smooth muscle cells of blood vessels, which suggested that the hemogenic role of biomechanical stretching and Piezo1 activation is intrinsic to AGM-endothelial cells.

Biomechanical stretching of blood vessels could activate Piezo1, Trpv4, K1-family members, as well as DEG/ENaC channels. Both Piezo1 and Trpv4 activation stimulated the endothelial-to-hematopoietic transition. However, only Piezo1 inhibition attenuated the stretch-mediated hemogenic effect, which suggested that Piezo1 and Trpv4 may have partially redundant roles.

Dnmt3b activation silenced the endothelial machinery to endow HSCs with self-renewal and multi-lineage reconstitution capacity. Although the inhibition of Dnmt3b reverts hematopoietic cells to phenotypic endothelial cells, these cells lacked functional endothelial properties. This suggested that the temporal and spatial role of Dnmt3b in the endothelial-to-hematopoietic transition was non-reversible. Biomechanical stretching or Piezo1 activation enhanced temporal and spatial expression of Dnmt3b without impacting Dnmt3a expression. The data demonstrated a distinction between the hemogenic role of Dnmt3b and the leukemic role of Dnmt3a during HSC development and differentiation.

The findings disclosed herein demonstrate how biomechanical forces stimulate cell fate transition and endow self-renewing capacity to stem cells by invoking epigenetic machinery. This study also provides a platform to derive LT-HSCs from pluripotent stem cells (PSC) or donor cell-derived endothelial or hemogenic endothelial cells. While a goal is to develop universally compatible HSCs, the bio-inspired bioreactor disclosed herein is a stepping stone when universally compatible, transgene-free source cells become available to treat patients with benign and malignant blood, metabolic, immune, and bone marrow diseases.

Materials and Methods

All procedures were approved by the Animal Care and Use Committees of Brigham and Women's Hospital and Boston Children's Hospital.

Mice were purchased Cd45.2 (C57BL6/J) and Cd45.1 (SJL) from The Jackson Laboratory and zebrafish morpholinos from GeneTools. Microangiography was performed by injecting fluorescent-labeled dextran dye in the atrium of zebrafish heart and its passage was recorded using live imaging. Immunostaining of zebrafish heart and mouse AGM were analyzed using an inverted fluorescent microscope. Cardiac tamponade, heart rate, and pulse frequency were analyzed in zebrafish embryos using bright field imaging or time-lapse confocal microscopy. The movement of red blood cells in blood vessels was analyzed as well as the endothelial-to-HSC transition in zebrafish transgenic embryos using time-lapse confocal imaging.

Pulsating blood vessels like conditions were stimulated in vitro using Flexcell FX-4000 machine. To analyze roles of pharmacological targets in regulating the endothelial-to-HSC transition, mouse embryo-derived AGM or whole mouse embryo were exposed ex vivo with biomechanical stretching, chemicals, or drugs. Next, hematopoietic colony formation assays were performed by incubating mouse AGM-derived cells in StemCell M3434 media for seven days. Serial transplantation of AGM-derived HSCs in lethally irradiated SJL mice were performed. The stem cell frequency upon biomechanical stretching was analyzed using a limiting dilution assay. To characterize properties of AGM-HSC-derived blood cells in primary transplants, percentage chimerism and reconstitution was measured using FACS, globin transcripts were analyzed using quantitative reverse transcriptase-PCR, myeloperoxidase amount was measured using PicoKine ELISA kit, TCR-β rearrangement was analyzed using PCR for TCR-β locus, pre-immune IG detection was analyzed using Thermo-Fisher Mouse Ig Isotyping kit, and delayed-type hypersensitivity was analyzed by injecting sheep RBC (Rockland Immunochemicals) in the footpad of pre-sensitized mice.

RNA-sequencing analyses were performed to measure gene expression patterns in mouse AGM treated with cyclic strain or pharmacological modulators. Using computational algorithms, hierarchical clustering was performed of differentially expressed genes as well as measured their overrepresented biological processes and pathways. Gene expression clusters of differentially expressed genes were analyzed and their mean expression level across cell populations compared. Next, Venn comparison of up- and down-genes was constructed to analyze candidate(s) important for cyclic strain- or pharmacological modulator(s)-mediated the endothelial-to-HSC transition. Furthermore, Dnmt3b and Dnmt3a protein expressions were analyzed in nuclear fractions of mouse AGM cells using EgiQuick assay kits. Data are presented as mean±s.d. unless otherwise noted. Statistical analyses were performed by paired or un-paired Student's t-tests. Significance was set at $P<0.05$.

Animals

Experiments used wild-type AB, Casper, and transgenic zebrafish lines lcr:eGFP, flk1:mCherry,flk1:eGFP, cd41:eGFP. Embryos were used up to 4 days pf. Experiments used Cd45.2 (C57BL6/J) and Cd45.1 (SJL) mice from The Jackson Laboratory.

Morpholinos

Morpholino antisense oligos were obtained (Gene Tools; sequences below) and injected into one-cell stage casper zebrafish embryos. Injected and uninjected embryos were incubated in E3 media at 28° C. until fixation.

cdh5-MO (5'-TACAAGACCGTCTACCTTTCCAATC-3'; SEQ ID NO:1)

sih-MO (5'-CATGTTTGCTCTGATCTGACACGCA-3'; SEQ ID NO:2)

piezo1-MO (5'-CAAAGTTCAGTTCAGCTCACCTCAT-3'; SEQ ID NO:3)
dnmt3bb.1-MO1 (5'-TTATTTCTTCCTTCCT-CATCCTGTC-3'; SEQ ID NO:4)
dnmt3bb.1-MO2 (5'-CTCTCATCT-GAAAGAATAGCAGAGT-3'; SEQ ID NO:5)

Chemical Treatment of Embryos

Zebrafish embryos were treated with the following chemical modulators in E3 fish media: 100 uM L-NAME (Fisher Scientific), 50 uM Digitoxigenin (Sigma), 25-50 uM Yoda1 (Cayman Chemical), 1 uM Nanaomycin (Nana; Fisher Scientific), 100 uM Gadolinium chloride ($GdCl_3$; Sigma), 5-10 uM 4α-phorbol 12,13-didecanaote (4Apdd; Sigma), or GSK205 (10 uM).

Microangiography

Fluorescent dye-labeled dextran beads were injected into the atrium of the control and cdh5-MO embryos, and captured real-time brightfield videos using a Nikkon SMZ1500 stereo microscope.

Heart Rate and Cardiac Output

Images of live zebrafish hearts were acquired on an Axioplan (Zeiss) upright microscope with a 5× objective lens using integrated incandescent illumination and a Fast-Cam-PCI high-speed digital camera (Photron) with a 512× 480 pixel grayscale image sensor. Images were obtained at 250 frames per second, with 1088 frames ('8 cardiac cycles) being acquired per condition. A custom software was used (implemented in MATLAB) to determine heart rate from sequential image files. Ventricular long and short axis were measured in both diastole and systole manually for each video using ImageJ and used to estimate chamber volume using standard geometric assumptions. A cardiac output was measured as diastolic minus systolic ventricular volume multiplied by heart rate (Shin et al., 2010), for at least ten embryos per morpholino dose.

Periodicity Analyses

Zebrafish Casper embryos were embedded in 0.8% low-melting-point agarose with tricaine (Sigma) and mounted in a petri dish. Next, a Nikon SMZ1500 stereomicroscope equipped with NIS Elements (Nikon) software was used to capture real-time brightfield videos of pulsating blood vessels in AGM region. The videos were used to quantify the pulse frequency in the blood vessels.

Brightfield Live Imaging

To perform brightfield live imaging, zebrafish Casper embryos were embedded in 0.8% low-melting-point agarose with tricaine (Sigma) and mounted in a petri dish. A Nikon SMZ1500 stereo microscope equipped with NIS Elements (Nikon) software was used to capture real-time brightfield videos and still images.

Confocal Microscopy cd41:eGFP were crossed with flk1:mCherry zebrafish and flk1:mCherry with lcr:eGFP zebrafish and injected morpholino in their transgenic embryos. Transgenic embryos were mounted in low-melting-point agarose and a spinning-disk confocal microscope was used to perform time-lapse confocal imaging of cd41:eGFP+ HSCs emerging from flk1+ endothelium from 30 to 42 hpf. The relative movement of lcr:eGFP+ red blood cells was analyzed in the context of flk1:mCherry+ endothelium. We performed image analysis using Imaris (Bitplane) software.

Whole-Mount In Situ Hybridizations

Whole mount in situ hybridizations was performed as previously described.

Cardiac Tamponade

A microinjection needle was used to puncture the pericardial sac and release the fluid built up around the heart of cdh5-MO-injected zebrafish embryos at 48 hpf.

Immunostaining

E10.5 chimeric mouse embryos were harvested, embedded in a paraffin block, transverse sections performed, and immunostained with primary antibodies Piezo1 (rabbit anti-mouse IgG; Abcam), Cd31 (donkey anti-mouse IgG; R&D Systems), c-Kit (rabbit anti-mouse IgG; R&D Systems), or Dnmt3b (donkey anti-mouse IgG; Abcam). and 4,6 diamidino-2-phenylindole (DAPI) antibodies as well as secondary antibodies Alexa Fluor 488 (donkey anti-rabbit IgG; Fisher Scientific) and Alexa Fluor 647 (donkey anti-goat IgG; Abcam) to detect their expression in the E10.5 AGM region.

Expression of flk1 (GFP), mf2 (mCherry), and DAPI (violet) were measured in hearts isolated from control and cdh5-MO silenced zebrafish embryos.

AGM Explants

E11.5 AGM were harvested from C57BL6/J Cd45.2 mouse embryos, and a single cell suspension of a three-embryo equivalent of cells was seeded on each well of a BioFlex six-well culture plate (FlexCell). We cultured cells overnight with the application of cyclic strain (Flexcell® FX-4000™ Tension System) and/or treatment with chemical modulators (25-50 μM Yoda1, 1 μM Nanaomycin, 100 μM $Gdcl_3$, 1 uM GsMTx4, 5-20 μM 4αPDD, 10 uM GSK205). Next, harvested cells were used to perform transplant, fluorescence-activated cell sorting (FACS) analysis, and colony-forming unit (CFU) assays.

Ex Vivo Incubation of the Embryos with Drugs

E11.5 mouse embryos were harvested from the uterus of the time-mated pregnant female, into sterile glass vials containing FBS, 1 mM glucose, 1% Penicillin-Streptomycin, and/or the selected chemical modulator (25-50 μM Yoda1, 1 μM Nanaomycin, 5-20 μM 4αPDD, or 10 uM GSK205). We placed glass vials in the ex vivo incubator (BTC Engineering, Cambridge, UK) consisting of a roller apparatus (rotating ~30 rpm), constant gas supply (21% $O_2$, 5% $CO_2$, balance $N_2$) and constant temperature at 37° C. After 24 hours, AGM were harvested to analyze the formation of hematopoietic cells by FACS and CFU assays.

Transplants

For primary transplantation, three-embryo equivalents of untreated or treated (cyclic strain or 25 μM Yoda1) AGMs plus splenic helper cells (~500,000 per mouse) were injected into lethally irradiated (split dose 10.5 cGy) Cd45.1 (SJL) mice by retro-orbital injection. For secondary and tertiary transplants, the bone marrow was isolated (legs, arm, pelvic bone, spine, sternum) from the transplanted mice. The bone marrow was loaded on a Ficoll gradient (Histopaque®-1083, Sigma-Aldrich), and the cells from the buffy coat incubated with biotin-conjugated lineage antibodies and streptavidin microbeads (Miltenyi Biotec). Next, the lineage negative (Lin−) cells were separated with MACS LS Columns (Miltenyi Biotec), and the donor Cd45.2 Lin−Sca1+c-Kit+ (LSK) cells sorted with a MoFlo Beckman Coulter sorter. Subsequently, the sorted Cd45.2 LSK cells were mixed with Cd45.1 splenic helper cells (~500,000 per mouse) and transplanted into Cd45.1 irradiated (split dose 10.5 cGy) SJL mice by retro-orbital injection.

Survival recipients were counted as a response for the limiting dilution assay: confidence interval of 1/(stem-cell frequency) was calculated by ELDA, according to Poisson distribution.

CFU and FACS Assay

For CFU assays, cells from AGM explant or ex vivo were plated in MethoCult GF M3434 media (StemCell Technologies). Seven days after seeding, we analyzed their capacity to make granulocyte, erythroid, macrophage, megakaryocyte (GEMM), granulocyte macrophage (GM), granulocyte (G), macrophage (M), and erythroid (E) colonies.

AGM cells from explants and ex vivo were stained with Sca1-Pacific-Blue (E13-161.7, Biolegend) and Flk1-APC-Cy7 (Avas 12α1, BD). Blood from transplanted mice was stained with the following antibody cocktail: Cd45.2-Pacific-Blue (104, Biolegend), Cd45.1-FITC (A20, Biolegend), Cd3-PE (145-2C11, Biolegend), Cd8-PE (53-6.7, Biolegend), Mac1-APC (M1/70, Biolegend), Gr1-APC (108412, Biolegend), Cd19-APC-CY7(6D5, Biolegend), B220-APC-CY7 (RA3-6B2, Biolegend).

Cells from the bone marrow, spleen, thymus, and lymph node from mice transplanted with E11.5 AGM cells were stained with the following antibody panels: Bone marrow LT-HSC: Cd45.2-FITC (104, Biolegend), Ter119-Biotin (TER-119 BD), Gr1-Biotin (RB6-8C5, BD), Cd5-Biotin (53-7.3, BD), Cd8a-Biotin (53-6.7, BD), B220-Biotin (RA3-6B2, BD), Streptavidin-Pacific Blue (eBioscience), Sca1-PE-CY7 (D7, eBioscience), cKit-APC (2B8, eBioscience), Cd48⁻APC-CY7 (HM48-1, BD), Cd150-PE-CY5 (TC15-12F12.2, Biolegend). Erythroid development RI-RV in bone marrow: Cd45.2-Pacific-Blue (104, Biolegend), Cd45.1-FITC (A20, Biolegend), Ter119-APC (TER-119, Biolegend), Cd71-PE (R17217, eBioscience). Bone marrow granulocytes: Cd45.2-Pacific-Blue (104, Biolegend), Cd45.1-FITC (A20, Biolegend), Gr1-PE, (RB6-8C5, BD); Mac1-APC (M1/70, Biolegend). Spleen, thymus and lymph nodes T Cells: Cd45.2-Pacific-Blue (104, Biolegend), Cd45.1-FITC (A20, Biolegend), Cd8-PE (53-6.7, Biolegend), Cd4-APC (RM4-5, eBioscience). Spleen, thymus and lymph node myeloid and B cells: Cd45.2-Pacific-Blue (104, Biolegend), Cd45.1-FITC (A20, Biolegend), Cd19-APC-CY7 (6D5, Biolegend), Mac1-APC (M1/70, Biolegend). We performed all FACS analyses on a BD Fortessa cytometer. We performed hematopoietic organ analysis after 16 weeks of transplant.

Quantitative Reverse Transcriptase-Polymerase Chain Reaction Analysis (qRT-PCR)

FACS was used to sort erythroid precursors (Cd45.2⁺, Ter 19⁺, Cd71⁺) from the unlysed bone marrow isolated from AGM-transplanted mice. Total RNA was isolated using the RNAeasy Minikit (QIAGEN) and cDNA synthesis performed using Superscript III (Invitrogen). Quantitative real-time PCR was performed using SYBR Green (QuantaBio) on an MX3000P machine with the indicated primers (Sankaran et al., 2009). We normalized the expression to that of glyceraldehyde-3-phosphate-dehydrogenase (Gapdh) (Ochida et al., 2010).

Myeloperoxidase (MPO) Expression

Neutrophils (Cd45.2⁺, Gr1⁺, Mac1⁺) were FACS sorted from the isolated bone marrow of 16 week-primary transplanted mice and cultured in IMDM with 10% FBS overnight (500,000 cells/mL) in 24-well plates. Supernatant was collected and the MPO concentration measured using the Mouse MPO/Myeloperoxidase PicoKine™ ELISA Kit (Boster). The MPO concentration was also measured in blood serum.

PCR Assay for TCR-β Rearrangement

T cells (Cd45.2⁺, Cd3⁺) and myeloid cells (Cd45.2⁺, Mac1⁺) were FACS sorted from the splenocytes of 16 week-primary transplanted mice. Next, genomic DNA was extracted, and PCR performed for DH β2.1-JH β2.7 rearrangements within TCR-β locus. Our samples were denatured (940 C, 1 min), annealed (63° C., 2 mins) and extended (72° C., 2 mins) for 35 cycles. Primers sequences are as follows: 5' of DH β2.1: 5'-GTAGGCACCTGTGGG-GAAGAAACT-3'; SEQ ID NO:6, and 3' of JH β2.7: 5' TGAGAGCTGTCTCCTACTATCGATT; SEQ ID NO:7 (Lu et al., 2017).

Pre-Immune Ig Detection

Blood serum was isolated from 16 week-primary transplanted mice and pre-immune Ig isotypes were quantified by a mouse Ig isotyping kit (Thermo Fisher).

Delayed Type Hypersensitivity

Transplant mice were sensitized with sheep red blood cells (sRBC, $10^9$ cells/mL, 50 μL per site, Rockland Immunochemicals) through subcutaneous (lower back) and intradermal injections (right footpad). After six days of sensitization, pre-sensitized mice were challenged with $2 \times 10^9$ sRBC/mL in the left footpad and an equal volume of PBS in the right footpad (as a control). After 48 hours of the challenge, the footpad thickness was measured with a microcaliper. We normalized percent change at day 6 with the pre-challenged thickness of each footpad.

DNA Methyltransferase Expression

Nuclear extracts from AGM explants were harvested using an EpiQuik Nuclear Extraction Kit (Epigentek Group Inc.). Dnmt3b and Dnmt3a protein levels were analyzed using a colorimetric EpiQuik Assay Kit (Epigentek Group Inc.), according to the manufacturer's instructions. Concentration of Dnmt3b and Dnmt3a is relative to 1 μg of nuclear extract proteins.

RNAseq and Computational Anlayses

Total RNA from E11.5 mouse AGM explant cultures was isolated (control, stretch, Yoda1 and 4αPDD conditions) with the RNAeasy MiniKit (QIAGEN). Our cDNA libraries were generated by BGI Americas Corporation and sequenced with a HiSeq4000 device (Illumina) at eight samples per lane. We mapped our sequenced read fragments to the mouse reference genome GRCm38 (ENSEMBL release 69) using the Genomic Short-Read Nucleotide Alignment program (version 2012-07-20). DESeq2 and DEXSeq were used to test for differential expression (FDR=0.1) and differential exon use, respectively. Gene expression clusters of differentially expressed genes were analyzed and their mean expression level across cell populations compared. Next, Venn comparison was performed of up- and down-genes to analyze candidate(s) important for cyclic strain- or pharmacological modulator(s)-mediating the endothelial-to-HSC transition. Specifically, we performed hierarchical clustering with bootstrap analyses using the gplots package (Warners et al., 2017) in R (R Development Core Team, 2012). For GO analysis, we tested for over-representation of our differentially expressed genes on GO categories or pathways using Fisher's exact test and corrected for multiple testing using the Bonferroni method. We performed GO term enrichment analyses as previously described using a P value of 0.001 as minimum for statistically significant enrichment.

Statistical Analyses

Data are presented as a mean±standard error of the mean (Mean±SEM) unless otherwise noted. Statistical analyses were performed by paired or un-paired Student's t-tests. Significance was set at $P<0.05$.

What is claimed is:

1. A method of preparing a population of hematopoietic stem cells (HSCs), the method comprising:
   providing a population comprising hemogenic endothelial (HE) cells, the population provided by isolating CD34$^+$ cells from embryoid bodies, the embryoid bodies being differentiated from human induced pluripotent stem cells (iPSCs); and
   contacting the population comprising HE cells with an effective amount of Yoda 1 in the absence of a transgene and under conditions sufficient for stimulating formation of HSCs.

2. The method of claim 1, further comprising, recovering the HSCs.

3. The method of claim 1, wherein the effective amount of the Yoda1 is in the range of 5 to 500 uM.

4. The method of claim 1, wherein the iPSCs are generated from source cells obtained from a subject.

5. The method of claim 4, wherein the source cells are obtained from a subject who has a blood, bone marrow, metabolic, or immune disease.

6. The method of claim 5, wherein the subject does not have a hematological malignancy.

7. The method of claim 4, wherein the population of HSCs are administered to a recipient, wherein the HSCs engraft in a hematopoietic niche and reconstitute to functional, multi-lineage adult blood.

8. The method of claim 7, wherein the source cells were derived from the recipient.

9. The method of claim 1, wherein the hematopoietic stem cells comprise long term hematopoietic stem cells (LT-HSCs).

10. The method of claim 1, wherein the method comprises providing the population comprising HE cells to a bioreactor with the effective amount of Yoda 1 under the conditions sufficient for stimulating formation of HSCs.

11. The method of claim 1, wherein the effective amount of the Yoda1 is in the range of 5 to 200 uM.

12. The method of claim 1, wherein the effective amount of the Yoda1 is in the range of 5 to 100 uM.

13. The method of claim 1, wherein the effective amount of the Yoda1 is in the range of 25 to 100 uM.

14. The method of claim 1, wherein the effective amount of the Yoda1 is in the range of 25 to 50 uM.

15. The method of claim 1, wherein the iPSCs are prepared from human leukocyte antigen (HLA)-modified cells.

16. The method of claim 1, wherein CD34$^+$cells are isolated from embryoid bodies at day 8 of iPSC differentiation.

17. The method of claim 16, wherein embryoid bodies are dissociated with trypsin.

18. The method of claim 1, wherein the conditions sufficient for stimulating formation of HSCs comprises contacting the HE cells with Y-27632, Thrombopoietin (TPO), IL-3, Stem Cell Factor (SCF), IL-6, IL-11, IGF-1, VEGF, bFGF, BMP4, and FLT3.

19. The method of claim 18, wherein the population comprising HE cells is contacted with an effective amount of Yoda 1 under conditions sufficient for stimulating formation of HSCs for at least 7 days.

20. The method of claim 19, wherein HSCs are recovered as floating cells.

* * * * *

SEQUENCE LISTING

<160> NUMBER OF SEQ ID NOS: 7

<210> SEQ ID NO 1
<211> LENGTH: 25
<212> TYPE: DNA
<213> ORGANISM: Artificial
<220> FEATURE:
<223> OTHER INFORMATION: morpholino oligo cdh5-MO

<400> SEQUENCE: 1
tacaagaccg tctacctttc caatc                                          25

<210> SEQ ID NO 2
<211> LENGTH: 25
<212> TYPE: DNA
<213> ORGANISM: Artificial
<220> FEATURE:
<223> OTHER INFORMATION: morpholino oligo sih-MO

<400> SEQUENCE: 2
catgtttgct ctgatctgac acgca                                          25

<210> SEQ ID NO 3
<211> LENGTH: 25
<212> TYPE: DNA
<213> ORGANISM: Artificial
<220> FEATURE:
<223> OTHER INFORMATION: morpholino oligo piezo1-MO

<400> SEQUENCE: 3
caaagttcag ttcagctcac ctcat                                          25

<210> SEQ ID NO 4
<211> LENGTH: 25
<212> TYPE: DNA
<213> ORGANISM: Artificial
<220> FEATURE:
<223> OTHER INFORMATION: morpholino oligo dnmt3bb.1-MO1

<400> SEQUENCE: 4
ttatttcttc cttcctcatc ctgtc                                          25

<210> SEQ ID NO 5
<211> LENGTH: 25
<212> TYPE: DNA
<213> ORGANISM: Artificial
<220> FEATURE:
<223> OTHER INFORMATION: morpholino oligo dnmt3bb.1-MO2

<400> SEQUENCE: 5
ctctcatctg aaagaatagc agagt                                          25

<210> SEQ ID NO 6
<211> LENGTH: 24
<212> TYPE: DNA
<213> ORGANISM: Artificial
<220> FEATURE:
<223> OTHER INFORMATION: synthetic primer 5' of DH beta 2.1: 5'

<400> SEQUENCE: 6
gtaggcacct gtggggaaga aact                                           24

<210> SEQ ID NO 7
<211> LENGTH: 25
<212> TYPE: DNA
<213> ORGANISM: Artificial

```
<220> FEATURE:
<223> OTHER INFORMATION: synthetic primer 3' of JH beta 2.7: 5'

<400> SEQUENCE: 7
tgagagctgt ctcctactat cgatt                                          25
```